United States Patent [19]
Gammill

[11] Patent Number: 6,033,635
[45] Date of Patent: Mar. 7, 2000

[54] METHOD AND SYSTEM FOR BISPHENOL A PRODUCTION USING WATER

[76] Inventor: Ben Gammill, 926 Springdale Rd., Austin, Tex. 78702

[21] Appl. No.: 09/185,947

[22] Filed: Nov. 4, 1998

Related U.S. Application Data

[62] Division of application No. 08/632,663, Apr. 15, 1996, Pat. No. 5,959,158.

[51] Int. Cl.⁷ ...................................................... B01D 9/00
[52] U.S. Cl. ......................................................... 422/245.1
[58] Field of Search .............................. 422/245.1, 250.1, 422/254, 261; 568/24, 716, 724, 727, 728

[56] References Cited

U.S. PATENT DOCUMENTS

| | | |
|---|---|---|
| 2,791,616 | 5/1957 | Luten, Jr. . |
| 3,219,549 | 11/1965 | Prahl et al. . |
| 3,290,391 | 12/1966 | Prahl et al. . |
| 3,326,986 | 6/1967 | Dugan et al. . |
| 3,535,389 | 10/1970 | De Jong . |
| 3,673,262 | 6/1972 | Prahl et al. . |
| 4,131,749 | 12/1978 | Kiedik . |
| 4,180,683 | 12/1979 | Mitchell . |
| 4,188,496 | 2/1980 | Jaquiss et al. . |
| 4,192,954 | 3/1980 | Barker et al. . |
| 4,209,646 | 6/1980 | Gac et al. . |
| 4,300,000 | 11/1981 | Reinitz . |
| 4,327,229 | 4/1982 | Mendiratta . |
| 4,346,247 | 8/1982 | Faler et al. . |
| 4,348,542 | 9/1982 | Serini et al. . |
| 4,351,966 | 9/1982 | Flock . |
| 4,354,046 | 10/1982 | Ladewig et al. . |
| 4,369,293 | 1/1983 | Heydenreich et al. . |
| 4,375,567 | 3/1983 | Faler . |
| 4,387,251 | 6/1983 | Meyer et al. . |
| 4,396,728 | 8/1983 | Faler . |
| 4,400,555 | 8/1983 | Mendiratta . |
| 4,401,792 | 8/1983 | Axelrod et al. . |
| 4,408,087 | 10/1983 | Li . |
| 4,423,252 | 12/1983 | Maki et al. . |
| 4,447,655 | 5/1984 | Mendiratta . |
| 4,461,915 | 7/1984 | Mendiratta et al. . |
| 4,464,487 | 8/1984 | Thomas et al. . |
| 4,469,838 | 9/1984 | Liu et al. . |
| 4,492,807 | 1/1985 | Aneja . |
| 4,507,509 | 3/1985 | Mendiratta et al. . |

(List continued on next page.)

FOREIGN PATENT DOCUMENTS

| | | |
|---|---|---|
| 0 039 845 B2 | 11/1981 | European Pat. Off. . |
| 3421949 A1 | 1/1985 | Germany . |

OTHER PUBLICATIONS

"Proposed Agitator Speed Change—Phenol–Bisphenol Crystallizers," Sep. 24, 1991, 3 pages.

A.W. Bamforth, A.M.I.Chem.E., "What's new in crystallization methods and apparatus?" Chemical processing 1966, 1 page.

"Crystallization," vol. 7, pp. 265, 268, 269, and 724.

Process Economics Program, SRI International, Yoshio Kosaka and Kenneth B. Sinclair, "Bisphenol–A From Phenol and Acetone With an Ion Exchange Resin Catalyst—Union Carbide Technology," Sep. 1982, 32 pages.

E.J. de Jong and S.J. Jancic, "Industrial Crystallization 78—Proceedings of the 7th Symposium on Industrial Crystallization," Warsaw, Poland, Sep. 25–27, 1978, 11 pages.

Dialog Search processed Apr. 12, 1996, 6 pages.

Moyers, "Process Optimization–Industrial Crystallization for Ultrapure Products", CEP, vol. 82, May 1986.

Matsuoka, et al., "Polymorphic Solid State Transformation of BPA Crystals,"pp. 1–6.

*Primary Examiner*—William Powell
*Attorney, Agent, or Firm*—Conley, Rose & Tayon, PC

[57] ABSTRACT

Methods/systems for making a relatively high-purity bisphenol A product from phenol and acetone. Controlled turbulence is used to form bisphenol A adduct solids having improved physical properties. Phenol is separated from the bisphenol A product while inhibiting decomposition of bisphenol A.

34 Claims, 9 Drawing Sheets

U.S. PATENT DOCUMENTS

| | | |
|---|---|---|
| 4,517,387 | 5/1985 | Matsunaga et al. . |
| 4,529,823 | 7/1985 | Mendiratta . |
| 4,533,764 | 8/1985 | Chang et al. . |
| 4,544,677 | 10/1985 | Allen et al. . |
| 4,584,416 | 4/1986 | Pressman et al. . |
| 4,590,303 | 5/1986 | Mendiratta . |
| 4,638,102 | 1/1987 | Little . |
| 4,657,890 | 4/1987 | Garces et al. . |
| 4,740,634 | 4/1988 | Gomes de Matos et al. . |
| 4,740,635 | 4/1988 | Gomes de Matos et al. . |
| 4,777,301 | 10/1988 | Olson . |
| 4,788,249 | 11/1988 | Maresca et al. . |
| 4,798,654 | 1/1989 | Iimuro et al. . |
| 4,822,923 | 4/1989 | Li . |
| 4,825,010 | 4/1989 | Li . |
| 4,861,919 | 8/1989 | Robbins et al. . |
| 4,876,391 | 10/1989 | Kissinger . |
| 4,880,884 | 11/1989 | Mullins et al. . |
| 4,920,200 | 4/1990 | Brunelle et al. . |
| 4,927,973 | 5/1990 | Dong et al. . |
| 4,931,146 | 6/1990 | Iimuro et al. . |
| 4,942,265 | 7/1990 | Iimuro et al. . |
| 4,950,804 | 8/1990 | Iimuro et al. . |
| 4,950,806 | 8/1990 | Iimuro et al. . |
| 4,954,661 | 9/1990 | Iimuro et al. . |
| 4,973,650 | 11/1990 | Peters . |
| 4,994,533 | 2/1991 | Mullins et al. . |
| 4,994,547 | 2/1991 | Brunelle et al. . |
| 5,015,784 | 5/1991 | Rudolph et al. . |
| 5,105,026 | 4/1992 | Powell et al. . |
| 5,164,464 | 11/1992 | Hefner, Jr. et al. . |
| 5,198,591 | 3/1993 | Kiedik et al. . |
| 5,210,329 | 5/1993 | Gomes de Matos et al. . |
| 5,214,083 | 5/1993 | Kodaira et al. . |
| 5,227,452 | 7/1993 | Earls et al. . |
| 5,243,093 | 9/1993 | Kissinger et al. . |
| 5,245,088 | 9/1993 | Fimuro et al. . |
| 5,260,017 | 11/1993 | Giles, Jr. . |
| 5,266,660 | 11/1993 | Hefner, Jr. et al. . |
| 5,269,887 | 12/1993 | Jakob et al. . |
| 5,284,981 | 2/1994 | Rudolph et al. . |
| 5,288,926 | 2/1994 | Patrascu et al. . |
| 5,324,864 | 6/1994 | Asaoka et al. . |
| 5,345,000 | 9/1994 | Moriya et al. . |
| 5,368,827 | 11/1994 | Moriya et al. . |
| 5,382,712 | 1/1995 | Asaoka et al. . |
| 5,399,784 | 3/1995 | Asaoka et al. . |
| 5,434,316 | 7/1995 | Kissinger . |
| 5,475,152 | 12/1995 | Kissinger et al. . |
| 5,475,154 | 12/1995 | Lundquist et al. . |

(a)

(b)

METHOD AND SYSTEM FOR BISPHENOL A PRODUCTION USING WATER

This application is a divisional of application Ser. No. 08/632,663 filed Apr. 15, 1996, now U.S. Pat. No. 5,959, 158.

BACKGROUND OF THE INVENTION

1. Field of the Invention

The present invention generally relates to methods and systems for producing relatively high-purity bisphenol A products. More particularly, in one embodiment of the invention, the methods and systems relate to making a bisphenol A product of at least 99 weight percent purity that is formed while decomposition of bisphenol A is inhibited. In another embodiment, the methods and systems relate to forming adduct solids that contain bisphenol A and have a length to width ratio of less than about 5:1. Either one of the embodiments may be used in conjunction with the other embodiment.

2. Description of the Related Art

Bisphenol A ("BPA") is an important raw material in the production of epoxy resins and polycarbonate resins. Bisphenol A may be produced by various techniques, but typically it is prepared in an acid-catalyzed, condensation reaction of two moles of phenol and one mole of acetone. Commonly-used catalysts include hydrochloric acid, a mixture of sulfuric acid and hydrochloric acid, and an acidic form of an ion-exchange resin. A secondary catalyst may be employed to shift the reaction toward the production of the p,p isomer and away from the production of the o,p isomer and other impurities. In the following description, it is to be understood that the term "bisphenol A" or "BPA" refers to the p,p isomer and not the o,p isomer, as the o,p isomer is considered an impurity. A BPA product having a purity of less than about 99.5 percent is usually unsuitable for making polycarbonates.

It is well known to practitioners of the art that exposure of bisphenol A to a temperature approaching or exceeding its pure melting point (about 157° C.) may cause partial decomposition of bisphenol A to form phenol and impurities such as isopropenyl phenol. Isopropenyl phenol is a highly reactive species that polymerizes to form color body precursors that may be oxidized to become color bodies. Color bodies are undesirable species that increase the yellowness index of polycarbonate resins. The yellowness index is a measure of the clarity of the resin. The clarity of the resin increases as the yellowness index decreases. Temperature-induced decomposition of bisphenol A intensifies when the molar concentration of phenol is less than that of bisphenol A, with the rate of decomposition increasing as the concentration of phenol decreases relative to the concentration of bisphenol A. Thus, it is advantageous to maintain the temperature below about 150° C. in any process step where the numbers of moles of bisphenol A present is greater than the number of moles of phenol present. Decomposition of bisphenol A increases as the time that the bisphenol A is exposed to a temperature above its pure melt point increases. "Heat history" refers to the amount of time that the BPA-containing medium has been exposed to temperatures in excess of the pure BPA melting point while the number of moles of bisphenol A present is greater than the number of moles of phenol present. Those skilled in the art recognize that the suitability of a bisphenol A product as a raw material to make polycarbonates and other selected materials is inversely related to its heat history. A significant heat history may render the bisphenol A product totally unsuitable for making polycarbonates and selected other materials.

Additionally, exposure of bisphenol A to oxygen and/or acidic species will tend to catalyze decomposition of bisphenol A. Therefore, a goal of practitioners of the art is to minimize the entry of oxygen and acidic species into the process. Small amounts of acidic species and oxygen are inevitably present in the process stream. Practitioners of the art tend to encounter problems when employing a vacuum system in the purification and/or recovery process, since such a system may promote air seepage into process streams, thereby providing additional oxygen for the formation of color body impurities.

The alcohol color is commonly used as a measure of the tendency of bisphenol A product used for making epoxy resins to increase the color of the epoxy resins. As the alcohol color of a BPA product decreases, the tendency of the BPA product to increase the color of an epoxy resin decreases. BPA products having an alcohol color greater than about 20 may be unsuitable as a raw material for some epoxy processes. The caustic color is commonly used as a measure of the tendency of bisphenol A product used for making polycarbonate resins to increase the yellowness index of the resins. As the caustic color of a BPA product decreases, the tendency of the BPA product to increase the yellowness index of a resin decreases. BPA products having a caustic color greater than about 15 tend to be unsuitable for making polycarbonates with low yellowness indexes.

In the preparation of bisphenol A by the reaction of phenol and acetone, practitioners of the art typically perform an initial purification step (i.e., the first adduct crystallization step) in which an adduct solid (i.e., adduct crystal) is formed that has a substantially equal number of moles of bisphenol A and phenol.

Some methods relate to recovering a bisphenol A product directly from the BPA-phenol adduct crystal without further intermediate purification steps. Bisphenol A product is then typically recovered. Often, these methods involve a second adduct crystallization to produce an intermediate grade product from the mother liquor (i.e., from the liquid effluent in the first adduct crystallization step) that failed to solidify in the first adduct crystallization. The intermediate grade solids are then typically recycled into the feed stream of the first adduct crystallization zone to increase the bisphenol A concentration in the feed stream and to increase the amount of bisphenol A relative to impurities in the first adduct crystallization zone.

Some methods relate to melting the adduct crystal to form a melt, and then stripping phenol from the melt in a falling film still or wiped film evaporator.

The-above-described methods typically operate under a vacuum at a pressure of about 30–50 torr and expose bisphenol A to a temperature of about 180–200° C. Trace amounts of phenol are then removed by steam stripping at a temperature typically about 180–200° C., leaving a bottoms product melt termed "crude bisphenol A." The crude bisphenol A is then further purified in a medium other than phenol, with the medium typically being an organic solvent. Typically, the crude bisphenol A is crystallized from the medium, and then the bisphenol A product is typically melted and subjected to a distillation procedure to remove residual solvent from the melt before a bisphenol A product is recovered.

Some methods relate to redissolving the adduct crystals in clean phenol and again extracting a bisphenol A adduct crystal in a second crystallization step. Phenol may then be removed using a falling film still or wiped film evaporator, and a steam stripper, at temperatures as described above. The remaining finished bisphenol A is then solidified in a prilling or flaking process. Such prilling and flaking processes are well known in the art.

A variety of techniques exist for the recovery of a sufficiently pure bisphenol A product for use in polycarbonates, however it is believed that all such processes used by practitioners of the art expose bisphenol A to a temperature above at least 160° C.

Chang et al. (U.S. Pat. No. 4,533,764) appear to disclose a method directed to "removing the remaining small quantities of solvent to a parts per million level", the solvent being "occluded solvent" that is present in bisphenol A "produced from solvent crystallization." Chang et al. mention solvents including methanol, acetone, methyl formate, benzene, toluene, xylene, 2-propanol, chloroform, methylene chloride, ethylene dichloride, and trichloroethane, however phenol is not stated as a solvent applicable to the Chang et al. process.

Iimuro et al. (U.S. Pat. No. 4,931,146) appear to disclose a process for obtaining high-priority bisphenol A by removing phenol from an adduct of bisphenol A with phenol and removing continuously the residual phenol by steam stripping, wherein a multi-tubular packed column is used as stripping equipment. The method of Iimuro et al., however, appears to subject bisphenol A to high temperatures (160–200° C.) during the removal of phenol.

Jakob et al.(U.S. Pat. No. 5,269,887) appear to disclose a method in which phenol is removed from a BPA-phenol adduct using solid phase drying (sublimation). The method of Jakob et al., however, employs a vacuum. This vacuum tends to promote air seepage into the process. A goal of practitioners of the art is to minimize oxygen exposure in the system to prevent the formation of color bodies.

A number of other patents appear to be directed at purifying bisphenol A, including U.S. Pat. No. 4,354,046, U.S. Pat. No. 3,673,262, U.S. Pat. No. 3,290,391, U.S. Pat. No. 3,219,549, U.S. Pat. No. 2,791,616, U.S. Pat. No. 3,326,986, U.S. Pat. No. 3,535,389, and U.S. Pat. No. 5,475,152. It is believed that the solvent leaching techniques presented in many of these references are typically performed subsequent to a high temperature distillation step in which a crude bisphenol A product is obtained. Such leaching techniques alone are believed to be insufficient to produce a bisphenol A product of adequate purity for use in polycarbonate resins.

All of the above-mentioned patents are herein incorporated by reference.

Adduct solids of bisphenol A have a natural tendency to grow in a long, slender shape. Practitioners of the art typically produce bisphenol A solids with a length to width ratio of at least 5:1. In the preparation of adduct solids that contain bisphenol A, the formation of "short," "fat," robust solids with the lowest possible length to width ratio is preferred to allow the formation of a stable and porous cake during recovery of the solids. As the porosity of the solids cake increases, the cake wash efficiency is increased and the deliquoring properties of the cake are enhanced. Practitioners of the art aim to create a gentle environment for solidification in order to prevent breakage of the solids. In addition, a gentle environment avoids turbulence that may induce secondary nucleation. Secondary nucleation tends to result in the formation of "fines." "Fines" are relatively small (e.g., less than 20 micron average width), undesirable solids that promote the formation of a tight, compact cake with poor deliquoring and wash characteristics. Tight, compact cakes have a large surface area to volume ratio and tend to hold excessive amounts of liquor. Practitioners aim to create larger solids to inhibit compacting of the recovered solids cake. To achieve the formation of larger solids, practitioners of the art maintain a low stream velocity in their crystallizers to prevent turbulence and breakage of the formed solids. Additionally, some practitioners of the art remove acetone and water from the composition from which the BPA-phenol adduct solid is formed. Acetone and water are removed from the composition prior to its introduction into a solidification unit where the adduct solid is formed. An effect of the removal of acetone and water is a significant increase in the viscosity of the composition, which impedes the formation of turbulence in the solidification unit.

SUMMARY OF THE INVENTION

One embodiment of the invention relates to making a bisphenol A product of greater than about 99 weight percent purity that is formed in a process where decomposition of the bisphenol A is inhibited. Phenol and acetone may be reacted, resulting in a reactor effluent that includes bisphenol A, phenol, unreacted acetone and water produced by the reaction. The effluent may be directed to a first solidification system and then a first recovery system where a solid (e.g., adduct) of bisphenol A and phenol is obtained. Water (e.g., liquid or steam) may be added to the adduct to form an adduct solution with a lower melting point than the adduct solid. The adduct solid may be melted before such water is added. Phenol may be removed from the adduct solution in a column at a temperature below about 150° C. to inhibit the decomposition of bisphenol A to color body precursors. The pressure of the column is preferably greater than atmospheric to avoid air seepage into the system that may oxidize any color body precursors present in the system. The column bottoms stream preferably contains less than about 1 weight percent phenol, and at least a portion of it is preferably directed to the second solidification system and second recovery system where a bisphenol A product is obtained that contains at least about 99 weight percent bisphenol A.

Another embodiment of the invention relates to forming "solids" that contain bisphenol A and have a mean length to width ratio of less than about 5:1. It is to be understood that "solids" refers to useful, growth solids such as crystals and the like. Phenol and acetone may be reacted, resulting in a reactor effluent that includes bisphenol A, phenol, unreacted acetone and water produced in the reaction. The effluent may be passed through a solidification chamber. The turbulence of the stream in the chamber is preferably monitored. The turbulence of the stream is also controlled to allow sufficiently turbulent flow to fragment first solids to initiate the formation of second solids having a length to width ratio of less than about 5:1. The turbulence may also be controlled to inhibit or prevent: (a) substantial secondary nucleation from being induced by the turbulence, (b) a fouling rate of a cooling surface to exceed a specified rate, and/or (c) formation of fines. A portion of the stream preferably exits the chamber into a recovery system where the solid product is preferably separated and washed. The portion of the stream that is not recovered as a solid product is preferably directed to a drying column where acetone and water are removed. The drying column is preferably located downstream of the first solidification system so that the viscosity of the reactor effluent is not increased prior to the introduction of the effluent into the solidification chamber.

The above-mentioned embodiments may be used in combination with one another. In another embodiment, the above-mentioned improved solidification method may be employed to make the BPA-phenol adduct in the above-mentioned method of making a bisphenol A product of at least a purity of 99 weight percent while inhibiting the decomposition of bisphenol A.

An advantage of an embodiment of the invention is that it can be used to make a bisphenol A product of at least 99 weight percent bisphenol A that has no heat history.

Another advantage of the invention is that it may be used to reduce the melt point of a BPA-phenol adduct solid, allowing the removal of phenol in a column at a pressure of at least atmospheric pressure and at a lower temperature than is possible in conventional processes.

Another advantage of the invention relates to improving the physical properties of bisphenol A adduct solids.

Yet another advantage of the invention relates to decreasing the rate of fouling in a bisphenol A solidification system to improve production capacity of the system.

Still another advantage of the invention relates to maintaining a favorable stream viscosity to facilitate creation of a selected amount of controlled turbulence in a bisphenol A solidification system.

Another advantage of the invention relates to reducing the concentration of trace acids and chlorides in an adduct solution with an anionic exchange resin.

Yet another advantage of the invention relates to substantially eliminating the presence of fines in a bisphenol A solidification unit without adding heat to the system.

Further advantages, and novel features are provided in the following detailed description and will become apparent to those skilled in the art.

DETAILED DESCRIPTION

This invention generally relates to methods, systems and apparatus for making a relatively high purity bisphenol A product.

Figure 1:
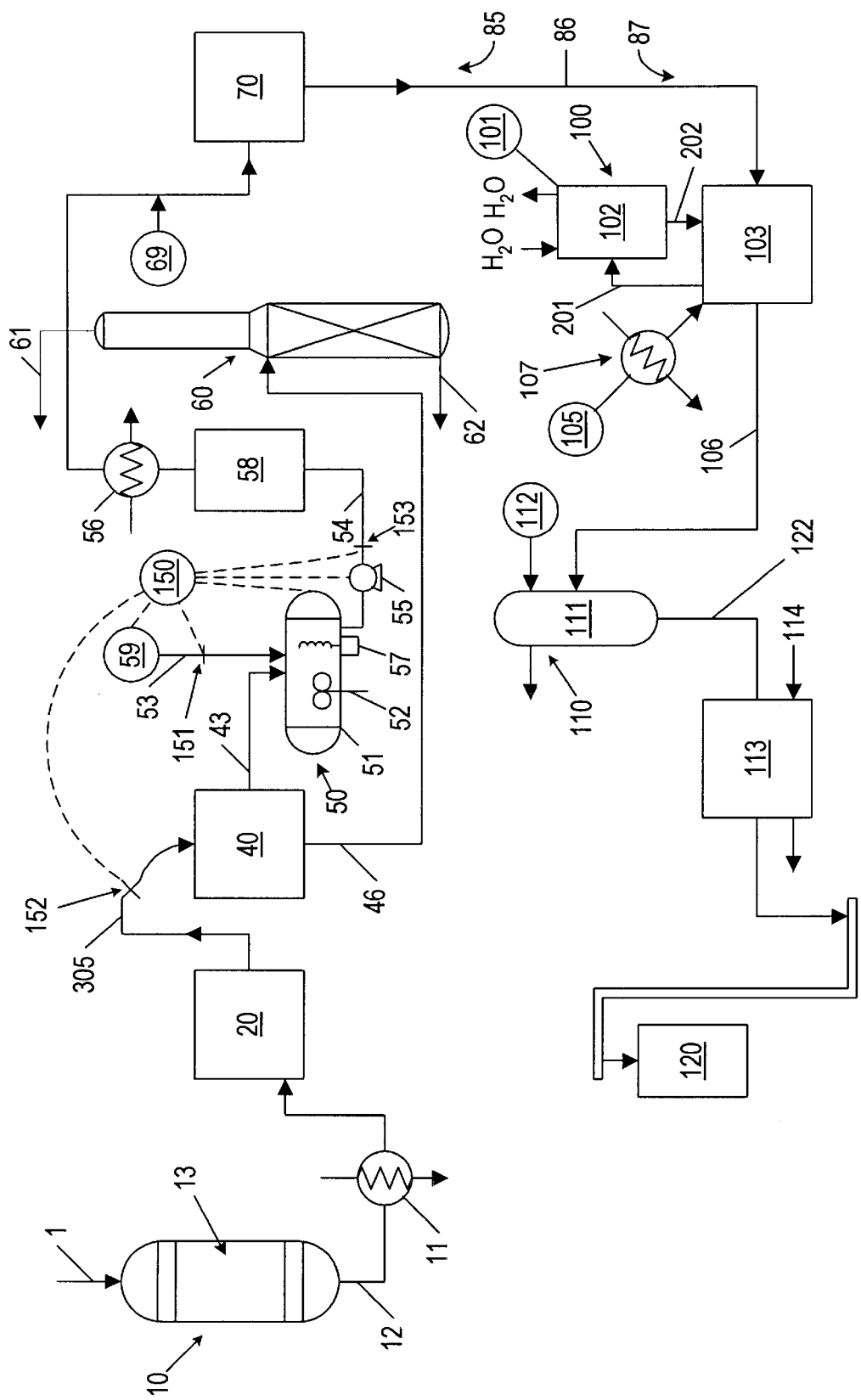
FIG. 1 is a flow diagram illustrating various embodiments of the invention.

Referring to FIG. 1, in an embodiment, mixture 1 of phenol and acetone is introduced into a reactor 10. Mixture 1 preferably may be at a temperature ranging from about 60° C. to about 65° C. Mixture 1 may be introduced into a reactor system that includes more than one reactor 10, and the reactors may be arranged in parallel, series, or in parallel trains, the trains including reactors connected in series.

Reactor 10 preferably contains an ion-exchange (e.g., cation) resin catalyst in the form of beads, although the reaction of phenol and acetone to produce bisphenol A may be accomplished by various other catalysts well known in the art. Ion-exchange resin 13 may absorb a significant amount of color bodies and other impurities. Water may also be absorbed by resin 13 causing it to swell and dump amounts of color bodies and other impurities into the process stream. The amount of water entering reactor 10 in mixture 1 is preferably minimized, since an additional amount of water is formed during the reaction of phenol and acetone. In an embodiment, the mixture 1 preferably contains less than 0.1 weight percent water. The reaction of phenol and acetone is exothermic, however reactor 10 is preferably operated so that the heat generated during the reaction causes the reactor effluent to emerge at a temperature below about 75° C. When reactor effluent 12 is at a temperature greater than about 75° C., cooler 11 may be required to cool the effluent to allow effective operation of first solidification system 20. In an embodiment, mixture 1 flows vertically through the reactor in a direction from the bottom of the reactor to the top of the reactor. Acetone is preferably maintained in slight stoichiometric excess of bisphenol A formed in reactor 10 to inhibit the formation of additional impurities, thereby inhibiting a corresponding decrease in BPA formation. Reactor effluent 12 includes bisphenol A, phenol, and preferably less than about 3 weight percent (and more preferably, less than about 1 weight percent) each of water and acetone.

Practitioners of the art typically purge at least a portion of heavy process impurities when they reach or exceed a predetermined level in reactor 10. The purge commonly is withdrawn from a stream that is recycled to the reactors. In an embodiment of the invention, the level of impurities is allowed to build until it reaches or exceeds an equilibrium level. The equilibrium impurity level is reached when about 1 part of impurities is present for an amount of bisphenol A between about 1.4 and 2.0 parts. While the level of impurities is at or in excess of the equilibrium level, few or no new impurities will be formed in the reactor. The level of impurities may approach the equilibrium level if impurities rearrange to form BPA, and the level of impurities may fall below the equilibrium level if impurities leave the process in a bisphenol A product. A relatively small amount of new impurities may form to replace the impurities that have rearranged to form BPA or that have exited the process in a BPA product. Ion-exchange resin 13 is preferably capable of absorbing impurities for a substantial time period before regeneration or replacement of the resin is necessary. In one embodiment, the purging of impurities and replacement or regeneration of the ion-exchange resin each occur once per year of operation. Purging less frequently than is done in conventional methods substantially decreases the mass of impurities formed, hence decreasing the mass of impurities that must be treated. Additionally, reducing the mass of impurities formed tends to increase the mass of product BPA that can be produced per unit mass of mixture 1.

Figure 2:
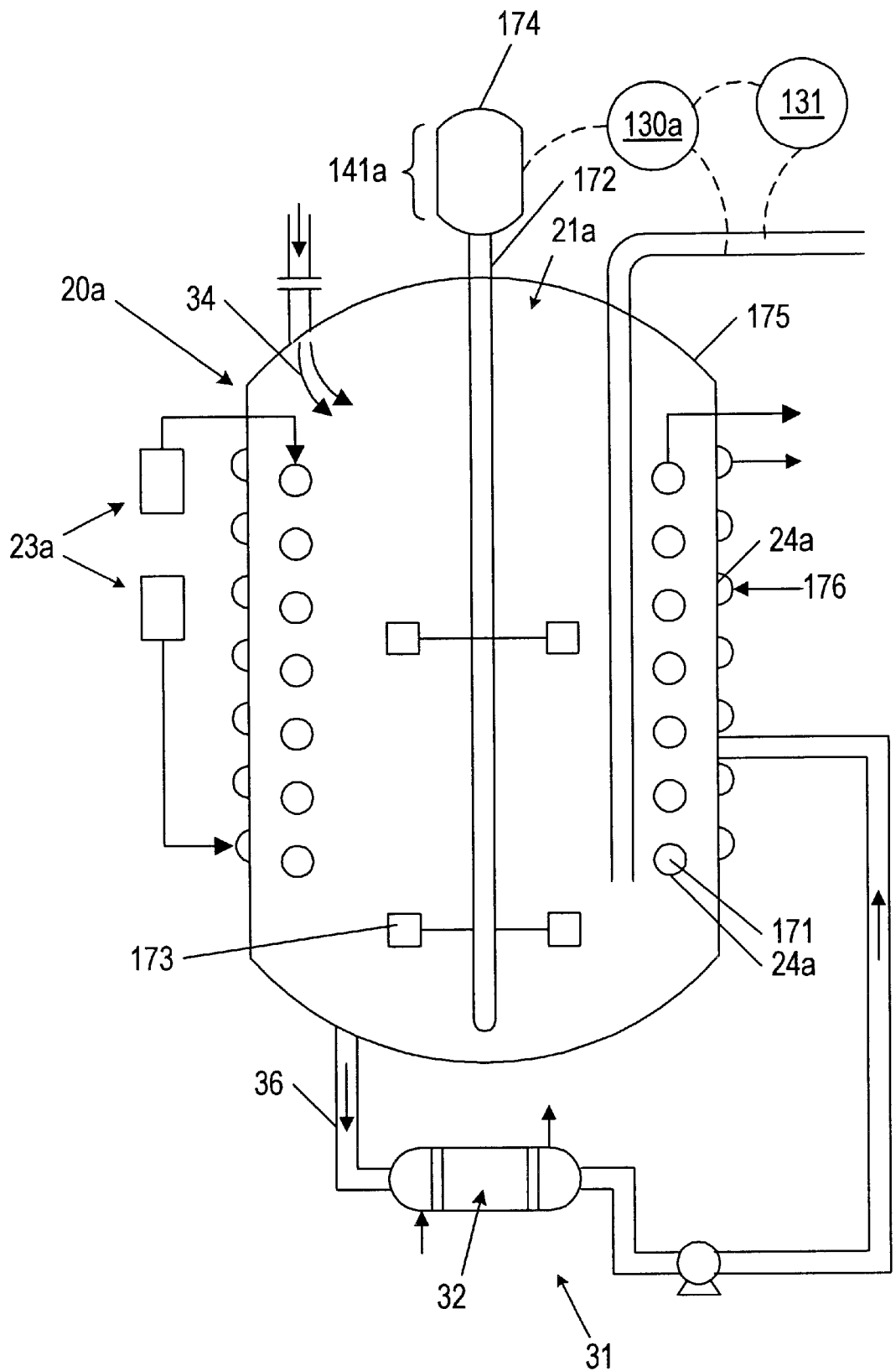
FIG. 2 is a schematic diagram of an embodiment of a solidification system.
Figure 3:
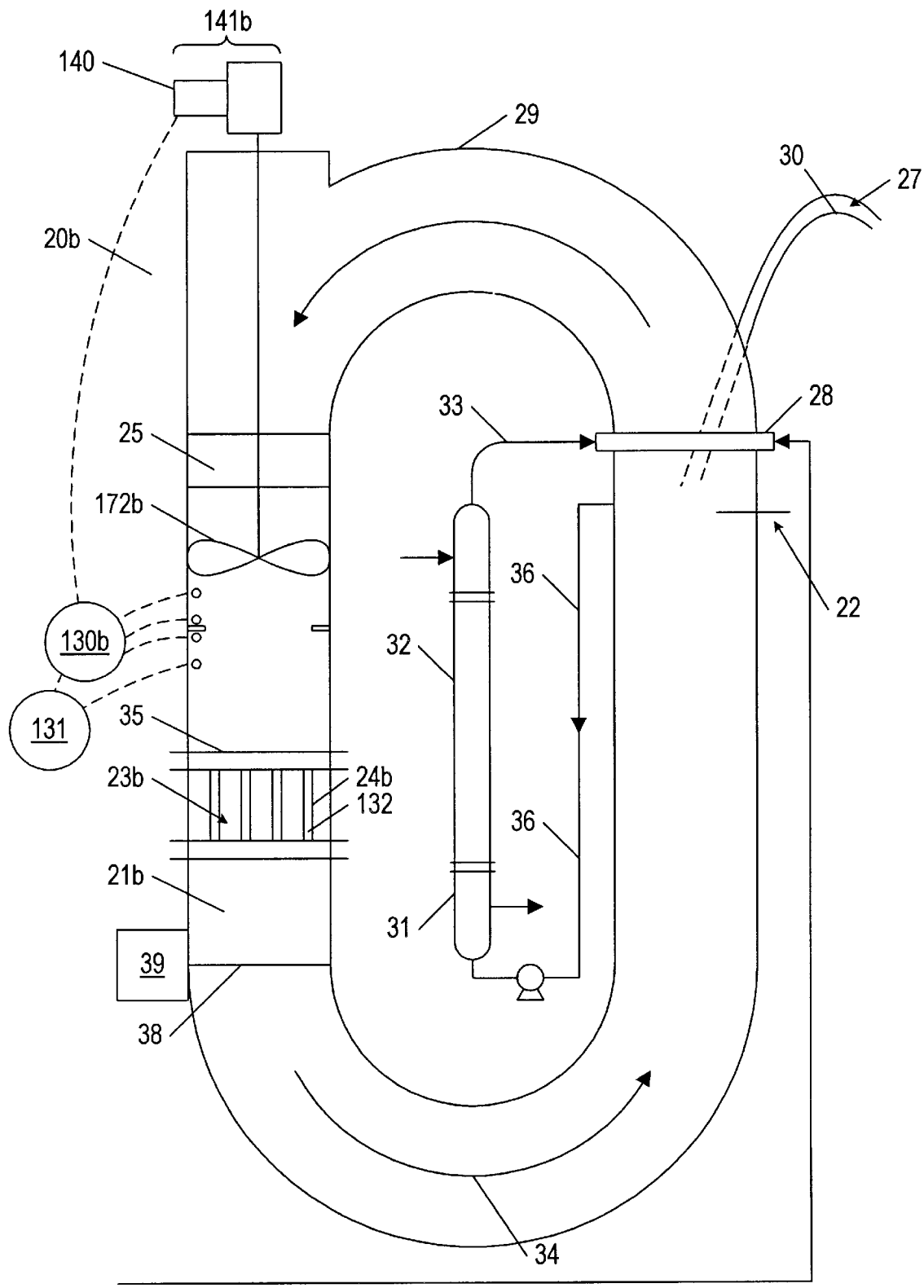
FIG. 3 is a schematic diagram of another embodiment of a solidification system.

In an embodiment, reactor effluent 12 is directed to first solidification system 20. A number of embodiments of solidification system 20 are illustrated in FIG. 2 and FIG. 3. Solidification system 20 preferably includes a solidification chamber 21 within which stream 34 is substantially continuously stirred, agitated, or circulated. In an embodiment, the solidification chamber includes a conduit loop. Such a solidification chamber (e.g., conduit loop) applicable to methods of the present invention is available from Messo-Chemietechnik in Duisburg, Germany. Within the solidification chamber is a solidification zone, a region where solids may form in stream 34.

The solidification zone occurs where stream 34 is "supersaturated" with bisphenol A. "Supersaturation" of stream 34 with bisphenol A means that an excess of bisphenol A is present in stream 34 such that not all of the bisphenol A present can dissolve in stream 34. Supersaturation also generally means that the stream is below its "cloud point" with respect to bisphenol A. As the temperature of stream 34 is lowered, the solubility of bisphenol A in the stream will decrease. The "cloud point" of a stream is the temperature at which the formation of solids in the stream may first be visually observed.

The formation of solids in stream 34 will cease without supersaturation. As such, the formation of solids in stream 34 will cease when an amount of bisphenol A solidifies and causes the concentration of bisphenol A in the fluid phase to fall below a concentration range necessary for supersaturation.

The formation of solids will also cease if the stream temperature rises above the cloud point. Such a temperature rise may be due to heat generated by solidification and/or the inflow of feed at a temperature above the cloud point. In an embodiment, the solidification zone includes substantially all points where stream 34 is present in solidification chamber 21a. In an embodiment, solidification chamber 21b is of sufficient length to allow stream 34 to fall essentially to the level of bisphenol A saturation in the conduit loop at point 22, located immediately before the feed enters first solidification system 20 through feed conduit 28.

Practitioners of the art typically aim to maintain a concentration of bisphenol A of below about 20 weight percent in the feed stream to solidification system 20. In an embodiment of the invention, however, the feed stream to solidification system 20 includes about 30 weight percent bisphenol A, about 50 weight percent phenol, and about 20 weight percent impurities. Methods of the present invention allow the formation of a sufficient amount of solids having a desirable shape using the feed compositions described above as well as many other feed compositions.

In an embodiment, cooling system 23b includes cooling surface 24b and is employed within the solidification chamber to remove heat from the chamber such that the temperature of stream 34 within the solidification zone is controlled within a predetermined range (i.e., between about 40° C. and about 55° C.). In an embodiment, cooling system 23b includes a shell and tube heat exchanger, and stream 34 preferably flows through the tubes 132 of the exchanger, with a cooling fluid flowing through the shell side. In an embodiment, solidification system 21a preferably includes a vessel 175 with a cooling surface 24a (located, e.g., on cooling coil 171) located within the vessel. In an embodiment, solidification system 21a includes a vessel with a cooling surface 24a (located, e.g., on cooling coil 176) located on the exterior of the vessel. In each of the above embodiments, the cooling fluid is preferably water, although any of a number of cooling fluids may be used. A number of other cooling systems may be used within solidification system 20. Preferably stream 34 is maintained at a temperature above 40° C. to prevent freezing of phenol, which has a pure melt point at about 41° C.

Some practitioners remove a significant portion of the water and acetone in reactor effluent 12 prior to the entrance of the effluent into solidification chamber 21. Removing water and acetone from the stream increases the viscosity of the stream and decreases the solubility of bisphenol A in effluent 12. Hence, solidification cooling requirements tend to be decreased.

In an embodiment of the invention, however, water and acetone preferably remain in effluent 12 when it enters first solidification system 20. Bisphenol A is more soluble in effluent 12 prior to the removal of water and acetone from the effluent. Therefore, the cloud point temperature of effluent 12 may be reduced by the water and acetone remaining in effluent 12. Practitioners typically seek to minimize the amount of cooling required for solidification, however additional cooling may be required for solidification when acetone and water are allowed to remain in effluent 12. The presence of acetone and water in stream 34 reduces its viscosity, however, providing advantages as described below.

The turbulence of stream 34 is controlled as it passes through chamber 21. A significant embodiment of the invention relates to achieving and controlling turbulence in stream 34 to reach a selected level of turbulent flow that is sufficient to break or fragment a portion of solids in the stream. In an embodiment, driving system 141b controls the velocity of stream 34 to create turbulence in the stream as it passes through chamber 21b. In an embodiment, turbulence is created and controlled in stream 34 as it passes through chamber 21a using driving system 141a. Turbulence in stream 34 preferably occurs as the stream contacts the cooling surface 24a/24b. In an embodiment, turbulence is created and controlled in stream 34 as it passes within the tubes 132 of cooling system 23b. In another embodiment, turbulence is created and controlled in stream 34 as it passes over coil 171 in solidification chamber 21a. In yet another embodiment, turbulence is created and controlled in stream 34 as it contacts cooling surface 24a of both coil 171 and coil 176.

It is believed that creating and controlling turbulence in the manner described above is contrary to conventional wisdom. Practitioners typically aim to prevent solids from fragmenting to allow the formation of larger solids. The method of the present invention, however, relates to fragmenting a portion of the solids in chamber 21 known as "first solids." "First solids" are solids that have a tendency to fragment when subjected to the controlled turbulence generated in chamber 21 due to their relatively high length to width ratio (e.g., typically 6:1, 8:1, or greater). The relatively high length to width ratio imparts a low beam strength to first solids, making them susceptible to fracture in a direction parallel to their width. First solids are undesirable since they may fragment into smaller particles when subjected to the centrifugal forces of conventional solid-liquid separators. As such, first solids promote collapsing of the recovered solids cake, resulting in a denser cake with diminished washing and deliquoring efficiencies. First solids may include relatively large solids and/or relatively small solids, since a key feature contributing to collapse of a recovered solids cake is the shape (e.g., length to width ratio) of the solids within the cake.

"Second solids" are solids that have a stronger tendency to resist fracture when subjected to the turbulence in chamber 21 due to their relatively low length to width ratio. In an embodiment, the velocity and/or agitation of stream 34 is adjusted to achieve a controlled turbulence such that the first solids fragment, while the second solids remain intact. First solids may be repeatedly fragmented until second solids are produced from the fragments. The formed second solids may further develop in chamber 21, with their maximum overall growth tending to depend upon their width, since they will likely fracture if their length exceeds a certain multiple of their width.

The precise length to width ratio where fracture has a tendency to occur depends upon a number of system factors discussed in the following. The formation of an excessive amount of first solids at any time in chamber 21 is preferably prevented by the constant maintenance of controlled turbulence within chamber 21, with the turbulence preferably occurring at least at locations proximate to cooling surface 24. In an embodiment, the turbulence within chamber 21 is controlled such that first solids have a length to width ratio of greater than about 5:1 and second solids have a length to width ratio of less than about 5:1. In a more preferred embodiment, the turbulence is controlled such that first solids have a length to width ratio of greater than about 3:1 and second solids have a length to width ratio of less than about 3:1. In a still more preferred embodiment, the turbulence is controlled such that first solids have a length to width ratio of greater than about 2:1, and second solids have a length to width ratio of less than about 2:1.

Increasing the level of controlled turbulence tends to increase heat transfer from stream 34 to cooling surfaces 24a/24b, thereby decreasing the temperature difference between the cooling medium within cooling system 23a/23b and stream 34. The decreased temperature difference lessens the formation of solids on cooling surfaces 24a/24b, decreasing the rate of "fouling" on the cooling surfaces and the frequency with which chamber 21a/21b must be shutdown to melt solids from the cooling surfaces and/or walls of the chamber. "Fouling" is the depositing of material on a heat transfer surface. Such material tends to have a low thermal conductivity and provides a resistance to heat transfer, thereby lowering the efficiency of heat transfer to or from the heat transfer surface. When the level of fouling reaches a predetermined level, system 20 must be shutdown to remove deposits from cooling surfaces 24a/24b. Such shutdowns decrease the annual production of chamber 21a/21b, hence a decrease in the fouling rate on cooling surfaces 24a/24b will increase the production capacity of chamber 21a/21b.

In an embodiment, a system is adapted to determine the pressure differential at various time intervals between points in the solidification zone. Such pressure differentials may be used to estimate the rate of fouling on the cooling surfaces so that the turbulence of stream 34 may be adjusted accordingly. The system may include any number of pressure gauges well known in the art, and, optionally, a programmable computer connected via electronic lines to such gauges.

In an embodiment, a controlled level of turbulence is maintained to inhibit the fouling rate on cooling surface 24a such that chamber 21a is shutdown about once every 60 hours to remove deposits from the cooling surface. Such a shutdown frequency is an improvement over similar conventional solidification chambers that must be shutdown about every 6 hours. In an embodiment steam is passed through coil 171 and coil 176 for about 30 minutes during shutdown of chamber 21a to remove deposits from cooling surface 24a. In an embodiment, the removed deposits preferably remain in chamber 21a and serve to initiate solids formation once chamber 21a is restarted.

In an embodiment, a controlled level of turbulence is maintained to inhibit the fouling rate on cooling surface 24b such that chamber 21b is shutdown about once every 2–20 days to remove deposits from the cooling surface. Different systems may be shutdown once every 3–5 or 6–10 days. In an embodiment, stream 34 is heated to a temperature below about 135° C. in chamber 21b for about 30–45 minutes to remove deposits from cooling surface 24b. The exact temperature to which stream 34 is raised should be determined empirically. The temperature should not be raised too high such that stream 34 circulates around chamber 21b due to thermal effects. The level of stream 34 within chamber 21b is preferably sufficiently low to prevent overflow of stream 34 through conduit 27 due to expansion of the stream. The level of stream 34 within chamber 21b is preferably sufficiently high to immerse tubes 132 in the stream to prevent the partial melting of the deposits on tubes 132. If this partial melting occurs, phenol may be released from the deposits, leaving a pure bisphenol A deposit on tubes 132. The removal of a pure bisphenol A deposit from tubes 132 would require the temperature of stream 34 to be raised above about 157° C., tending to cause decomposition of the bisphenol A. In an embodiment, the removed deposits preferably remain in chamber 21b and serve to initiate solids formation once chamber 21b is restarted.

In an embodiment, the temperature of stream 34 within chamber 21 is gradually reduced to about 60° C. to initiate the formation of solids.

In an embodiment, the temperature difference between stream 34 and the cooling medium that contacts cooling surfaces 24a/24b is monitored to determine the fouling on cooling surfaces 24a/24b. The degree of fouling tends to be directly proportional to the increase in the temperature difference between stream 34 and the cooling medium for a selected amount of heat transfer. Thus, the temperature difference between stream 34 and the cooling medium that is required to cool stream 34 to a selected temperature will tend to increase over time as the degree of fouling on cooling surfaces 24a/24b increases. In an embodiment, the controlled level of turbulence is adjusted as a function of the temperature difference between the cooling medium and stream 34.

"Primary nucleation" is the formation of solids in a stream that proceeds due to the supersaturation level of a stream. Primary nucleation is preferable because it allows the formation and growth of solids to occur in an orderly manner. At excessive levels of turbulence, "secondary nucleation" and/or "spontaneous nucleation" may be induced and additional sites may become available for initiation of solids formation. "Secondary nucleation" is the formation of solids due to stresses present in a supersaturated stream. Such stresses may include shear stresses, impact stresses, and/or cavitation stresses. Secondary nucleation is undesirable because it promotes the formation of numerous fines, which provides additional sites and surface area for the growth of bisphenol A solids. The result is the development of solids at a greater number of smaller sites, which adversely affects the size distribution of the formed solids. The mean size of the solids will tend to decrease. "Spontaneous nucleation" is more severe than secondary nucleation and is characterized by the formation of an increased amount of fines, with most all of a dissolved solid (bisphenol A) contained in the stream solidifying to form fines. Spontaneous nucleation may be induced (a) by extreme levels of turbulence in a stream, (b) if the temperature of the stream falls too far below its cloud point, (c) or a combination thereof. The turbulence and/or temperature of stream 34 should be controlled to prevent inducement of significant secondary nucleation and/or spontaneous nucleation by the turbulence. In an embodiment, the velocity and/or agitation of stream 34 is controlled to attain as great a level of turbulence as possible without inducing significant secondary or spontaneous nucleation.

The optimum turbulence needed to achieve selected physical properties of the solids formed in stream 34 may vary among embodiments of the invention. The optimum turbulence depends on various system factors including: (1) the shape of solidification chamber 21, (2) the characteristics of any pumps or agitators used within solidification chamber 21, (3) the composition and temperature of stream 34, (4) the degree of supersaturation of bisphenol A in stream 34, (5) the viscosity of stream 34, and (6) the density of the formed solids. In an embodiment, the optimum turbulence is determined empirically in the following manner. With the system at equilibrium, selected physical properties of the solids formed in stream 34 are determined using an analyzer (e.g., analyzer 131). The physical properties that are determined using the analyzer preferably include the mean length to width ratio of the formed solids and the mean width of the formed solids. The analyzer also is preferably capable of revealing selected physical properties of individual solids, particularly the solids that have the greatest or least values for any of the selected physical properties. The analyzer preferably is adapted to automatically determine selected physical properties characteristics, however other devices adapted to analyze solids may be used as well. In one embodiment, a magnifying means may be used to visually observe the solids to determine physical properties of the solids. Upon determination of the selected physical properties, the turbulence of stream 34 is increased using a pump and/or agitator and/or other means known in the art. Screens, shakers, and/or weights may also be used. After the system has reached equilibrium, samples of the solids are analyzed to determine selected physical properties, and the turbulence in the stream is again increased. Secondary and spontaneous nucleation may be detected by analyzing the physical properties of solids. An increase in the presence of fines as the turbulence level increases is likely an indication of the presence of substantial secondary or spontaneous nucleation. After substantial secondary or spontaneous nucleation is detected, the turbulence of stream 34 is decreased to a level such that substantial secondary nucleation ceases. The turbulence should be repeatedly adjusted as a function of the selected physical properties of stream 34 as determined by the analyzer. Ultimately, a maximum level of turbulence should be achieved such that substantial secondary nucleation does not result from the turbulence. As the velocity of stream 34 is increased, the flow of coolant in cooling system 23a/23b may have to be increased accordingly. In one embodiment, the optimum turbulence is achieved in a stream having a velocity exceeding 6 feet per second.

Figure 5:
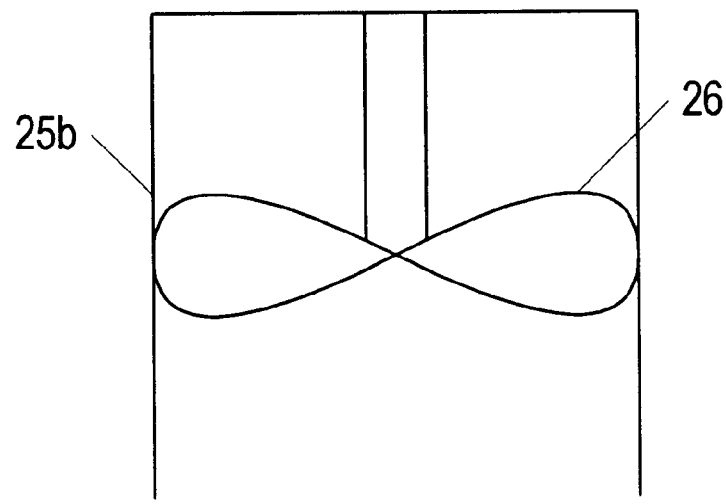
FIG. 5 is a schematic diagram of an embodiment of a pump.
Figure 6:
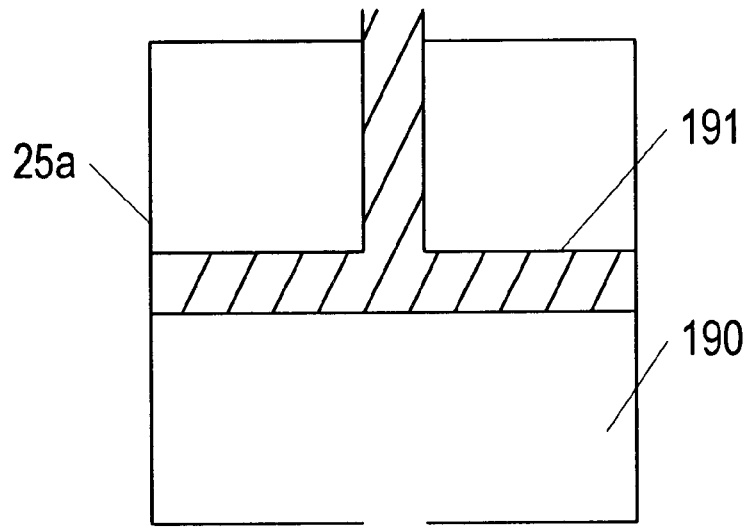
FIG. 6 is a schematic diagram of another embodiment of a pump.

In an embodiment, pump 25b having impeller 26 (shown in FIG. 5) and a variable speed motor 140 is used to pass stream 34 through solidification chamber 21b. The velocity and/or agitation of stream 34 is preferably controlled by adjusting the speed and/or size of impeller 26. In an embodiment, the control system is used to vary the speed of impeller 26. The control system preferably includes analyzer 131, which may include a screening system to size various solids. Analyzer 131 is used to determine physical properties of the solids formed in solidification chamber 21. Control system 130a/130b is adapted to send a signal to the variable speed motor to vary the speed of impeller 26 as a function of the physical properties of the solids. As the speed of impeller 26 increases, the flow rate and velocity of the stream are increased, thereby increasing the level of turbulence in the stream within solidification chamber 21. Control system 130a/130b may be used to continuously adjust the turbulence of stream 34 to attain preferred physical properties of the solids formed in the stream.

In an embodiment, pump 25 includes a chamber 190 and a piston 191 with a variable stroke length. The control system may be used to vary the stroke length. Analyzer 131 is used in the manner described above to determine the physical properties of the solids formed in solidification chamber 21. Control system 130a/130b is preferably adapted to send a signal to pump 25 to vary the stroke length as a function of the physical properties of the solids. As the stroke length increases, the flow rate and velocity of the stream are increased, thereby increasing the level of turbulence in the stream throughout solidification chamber 21. Control system 130a/130b may be used to continuously adjust the turbulence of stream 34 to attain preferred physical properties of solids formed in the stream.

In an embodiment, agitator 172 is used to create a selected level of turbulence in stream 34. Agitator 172 preferably includes a blade 173, but any agitating system well known in the art may be used. Agitator 172 may be the sole means by which the selected level of turbulence is created or it may be used in conjunction with other systems including pumps as described above. In one embodiment, the agitator includes a variable speed motor 174 and control system 130a that adjusts the speed of a blade 173 on agitator 172 as a function of selected physical properties of solids formed in stream 34. Such physical properties are preferably determined using analyzer 131 as described above.

A simpler control system may be used if the selected level of turbulence to achieve the preferred physical properties of solids is known. Any of a number of flow meters well known in the art may be used to determine the flowrate of the system. The velocity of stream 34 determined from the flowrate is compared to a selected velocity determined from the known selected turbulence. A manual or automatic control system 130 is used to adjust the turbulence of stream 34 by modifying the pumping and/or agitation rate to minimize the difference between the actual velocity of stream 34 and the selected velocity of stream 34.

In an embodiment, flow monitoring system 39 is used to determine the velocity or flowrate of stream 34 as it circulates through chamber 21. The velocity or flowrate may be used to estimate the turbulence level of stream 34, and the pumping rate of pump 25 may be adjusted to achieve optimum turbulence. In an embodiment, a flow monitoring system relays signals to control system 130a/130b, which sends a signal to variable speed motor 140 and/or agitator 172a/172b such that the velocity and/or agitation rate is adjusted to achieve a selected level of turbulent flow. In an embodiment, orifice plate 38 is used in conjunction with flow monitoring system 39.

Control system 130 may transmit signals that are digital or analog, and the signals may be converted from analog to digital or from digital to analog at multiple points in a control scheme. Feedback control may be employed in which the turbulence of stream 34 is adjusted as a function of system properties including: (1) the physical properties of the stream and/or the solids, (2) the fouling rate on cooling surface 24, (3) the determined level of secondary or spontaneous nucleation, and/or (4) a combination thereof. Feedforward control may be employed in which the turbulence of the stream is adjusted using a model that anticipates the physical properties of solids, fouling rate, or onset of substantial secondary or spontaneous nucleation. Such model would be determined empirically from the particular system that it predicts. A controller employing proportional control, differential control, integral control, or any combination thereof may be used in control system 130.

Referring to FIG. 1, water and acetone removal and recovery preferably begins in drying tower 60 downstream of first solidification system 20. Drying tower 60 is located downstream of system 20 so that the viscosity of effluent 12 is not increased before it enters chamber 21. The velocity that stream 34 must reach to achieve the selected level of turbulent flow tends to decrease as the viscosity of stream 34 decreases. The required pumping power tends to decrease both as the fluid viscosity decreases and as the necessary fluid velocity decreases. Thus, employing drying tower 60 downstream of system 20 facilitates the creation of the selected level of turbulence in chamber 21, and generally reduces the required pumping power to achieve that turbulence.

Some practitioners allow acetone and water to remain in effluent 12 and/or add water to effluent 12 prior to its introduction into a solidification unit. Such techniques are directed toward promoting crystal formation, however they fail to favorably alter the shape of the solids as in embodiments of the present invention. The mere addition of water will promote the formation of larger solids with an unchanged mean length to width ratio. Thus, the tendency of the solids to fragment when subjected to the centrifugal forces of solid-liquid separators will not be significantly lessened.

In an embodiment of the invention, however, the water content of effluent 12 is maintained to facilitate the creation of a selected turbulence level to alter the shape of formed solids.

Pump 25 is preferably located outside of the solidification zone. Generally, about 90% of any secondary nucleation that occurs typically will occur at the pump, however, no secondary nucleation can occur without supersaturation of stream 34. Therefore, locating the pump outside of the solidification zone may prevent a substantial amount of secondary nucleation from occurring. The solidification zone preferably extends from point 35 (immediately after stream 34 enters cooling system 23) to point 22.

In one embodiment of the invention, solidification chamber 21b includes a conduit loop having a portion of the conduit proximate to impeller 26 characterized by a reduced diameter relative to the remainder of the conduit diameter. A solidification chamber that has a venturi tube may be used to connect a conduit portion containing an impeller to a conduit portion of a much greater diameter. Enlarging the diameter of chamber 21b may increase the residence time of stream 34 in chamber 21.

In another embodiment of the present invention, the diameter of chamber 21b is substantially constant throughout the length of the chamber 21b, and the diameter is only slightly larger than the impeller diameter. It is anticipated that crystal growth will occur relatively rapidly upon the entrance of stream 34 into cooling system 23, and so increasing the diameter of chamber 21b is not preferable. The ease in which turbulence is achieved tends to increase as the diameter of the solidification chamber decreases.

In an embodiment, solidification chamber 21b includes slurry overflow 27. Stream 34 is preferably circulated through chamber 21b, with the rate of the feed entering the chamber through feed conduit 28 controlling the rate that stream 34 exits through slurry overflow 27. Slurry overflow 27 is preferably a conduit having an underside 30 of its top that is at an elevation slightly below the top 29 of the solidification chamber 21b. The fluid level in overflow 27 typically remains about equal to the fluid level in the solidification chamber. When the fluid level of the solidification chamber exceeds the bottom of the slurry overflow conduit 27, an amount of fluid will flow down the slurry overflow, exiting first solidification system 20 to enter first recovery system 40. In an embodiment, the elevation of the underside 30 of the top of slurry overflow 27 is between about 3 inches and about 12 inches below the elevation of top 29.

In an embodiment, first solidification system 20 includes a fines destruction or reduction system (see item 31). Fines system 31 directs a portion 36 of stream 34 through heating system 32 to heat portion 36 to a temperature slightly above the cloud point of stream 34. Heating system 32 is preferably a shell and tube heat exchanger, although any of a number of heating devices may be used. Steam is preferably used to heat portion 36, but numerous other heating media may be employed. The residence time of exchanger 32 and/or the temperature of the heating medium within exchanger 32 are preferably adjusted such that any fines that are present are melted completely, while larger solids are only slightly melted. Melting tends to initiate at the ends of the larger solids, in a manner such that the length to width ratio of the solids is decreased. In addition, first solids that are also fines tend to more strongly resist fracture than larger first solids having the same length to width ratio. Thus melting the fines tends to reduce the presence of fines. The fines tend to include a higher percentage of first solids than the larger solids formed in chamber 21a/21b. Therefore reducing fines tends to improve the mean length to width ratio of the formed solids. Thus, fines system 31 improves the physical properties of the solids by favorably modifying the shape of the larger solids in addition to reducing fines. Melting the fines also provides additional bisphenol A for the continued growth of the solids remaining in stream 34. In an embodiment, fines system 31 preferably draws portion 36 from chamber 21b near point 22, and effluent 33 is redirected into chamber 21b through feed conduit 28.

The above-mentioned embodiments may be used in combination with one another. For instance, in an embodiment, solidification system 20 includes: (a) a conduit loop and slurry overflow 27, (b) cooling system 23b including a shell and tube heat exchanger to remove heat from stream 34 to initiate solidification, (c) pump 25b with impeller 26 to circulate the stream around the conduit loop, and (d) fines system 31, each as described above. In another embodiment, solidification system 20 includes: (a) vessel 175, (b) coil 171 to remove heat from stream 34 to initiate solidification, (c) agitator 172 with blade 173 to circulate the stream over coil 171, and (d) fines system 31, each as described above. In another embodiment, solidification system includes (a) a conduit loop and slurry overflow 27, (b) cooling system 23 to remove heat from stream 34 to initiate solidification, (c) pump 25b with impeller 26 to circulate the stream around the conduit loop and create and control the level of turbulence in stream 34, (d) agitator 172 to create and control additional turbulence within stream 34 and (e) fines system 31, each as described above. First solidification system 20a (FIG. 2) is generally preferred over first solidification system 20b (FIG. 3). Numerous other combinations of embodiments described previously and below will become apparent to those skilled in the art.

The use of fines system 31 tends to reduce the presence of fines but also increases the duty of cooling system 23. Controlled turbulent flow serves to reduce the presence of fines. In an embodiment, the presence of solids having a width of less than 60 microns is substantially eliminated by the selection of a suitable turbulence level in stream 34 rather than the use of fines system 31.

Referring to FIG. 1, first recovery system 40 includes at least one solid-liquid separator 41 to recover an "adduct solids" of bisphenol A with phenol. In the context of this invention the word "adduct" means a physical association of two or more molecules. Such an association can be, for example, when a molecule of one component is either wholly or partly locked within the crystal lattice of the other. An "adduct solid" including bisphenol A and phenol means a solid in which bisphenol A and phenol are both physically associated within a solid.

First recovery system 40 may include a centrifugal filter system, a rotary vacuum filter system, or a pressure filter system. The filter systems may be batch, continuous, or a combination thereof. In an embodiment, a combination of rotary vacuum and pressure filter systems is used for enhanced wash efficiency, followed by a centrifugal filter system for deliquoring.

The adduct solid preferably contains bisphenol A and about 29–31 (e.g., 29.2) weight percent phenol, and more preferably bisphenol A and phenol in equimolar amounts. The adduct solid may contain more moles of phenol than bisphenol A due to any phenol residue remaining on the surface of the recovered adduct solid.

In an alternate embodiment, first recovery system 40 may include batch or continuous centrifugal filters, or rotary pressure or vacuum filters, any of the above being used singularly or in combination. Batch or centrifugal filters may be horizontal or vertical. Continuous centrifugal filters may be "pushers", etc. Rotary pressure or vacuum filters may be offered by Krauss-Maffei or Bird Machine Co. Preferably first recovery system 40 will include a wash system to wash crystals with phenol.

Figure 1A:
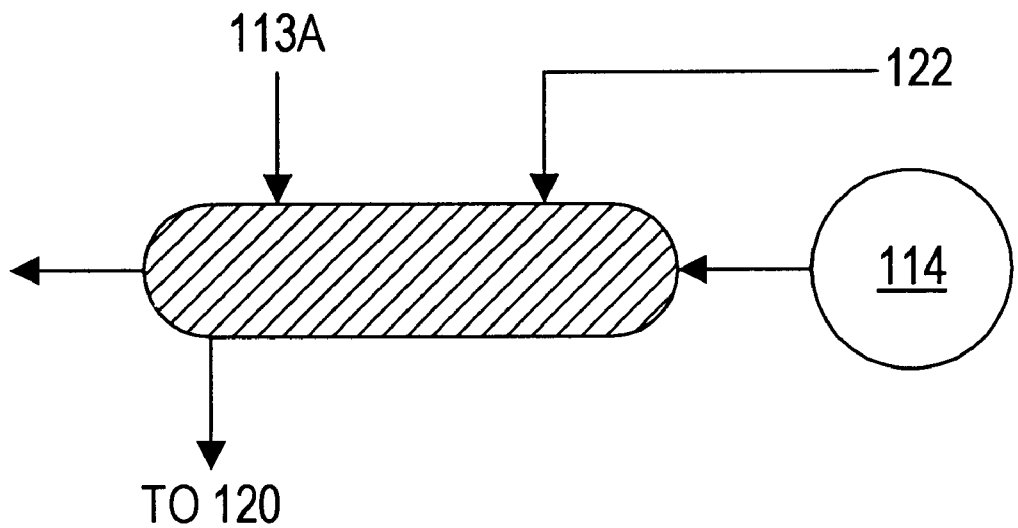
FIG. 1A depicts alternate embodiments of dryers.
Figure 1A:
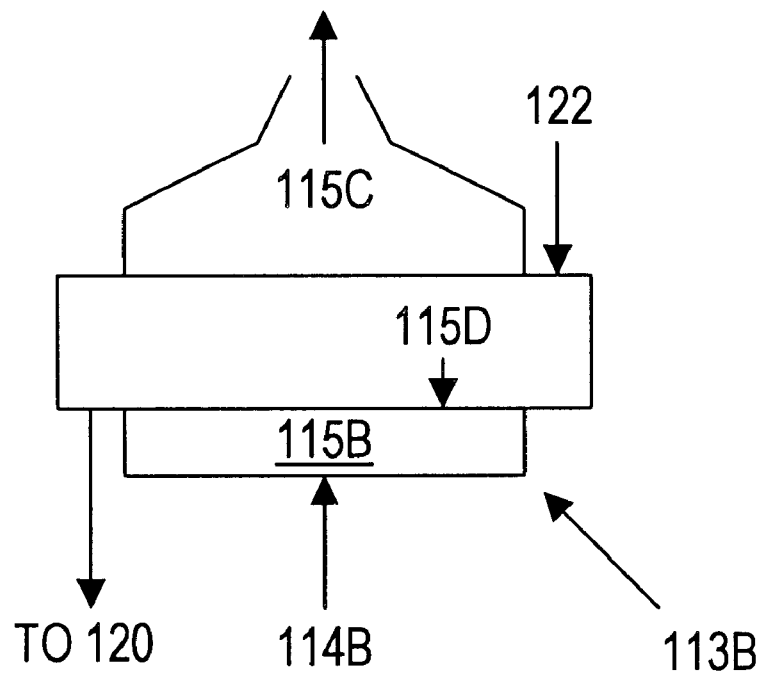
Figure 1B:
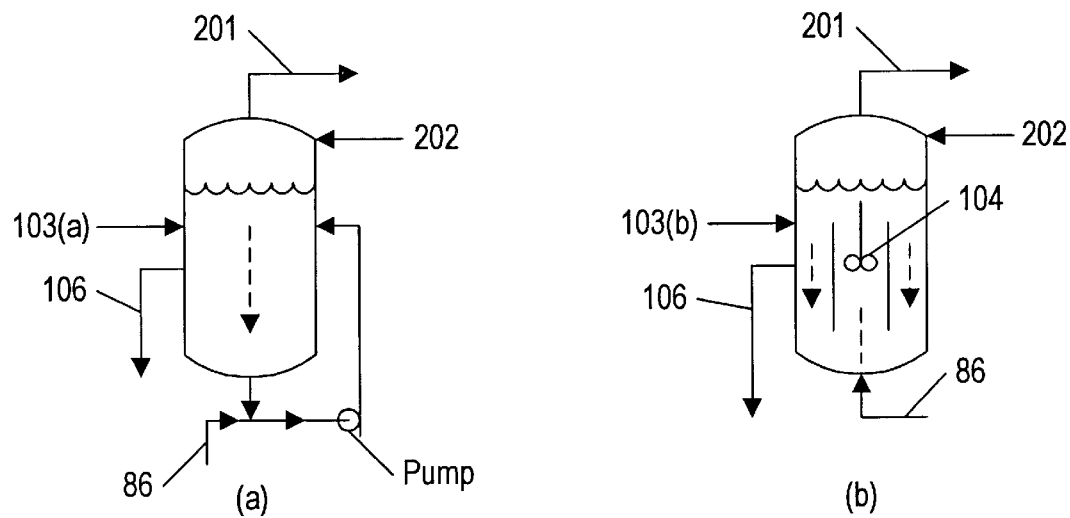
FIG. 1B (a–c) depicts alternate embodiments of crystallizers in a second solidification system.
Figure 1B:
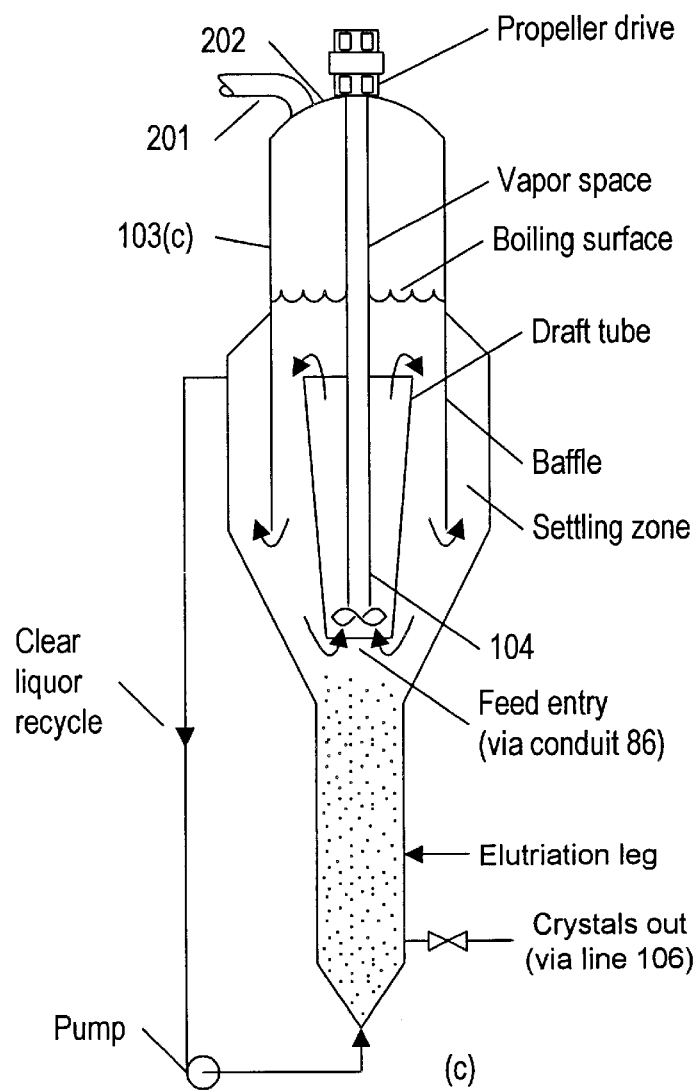
Figure 1C:
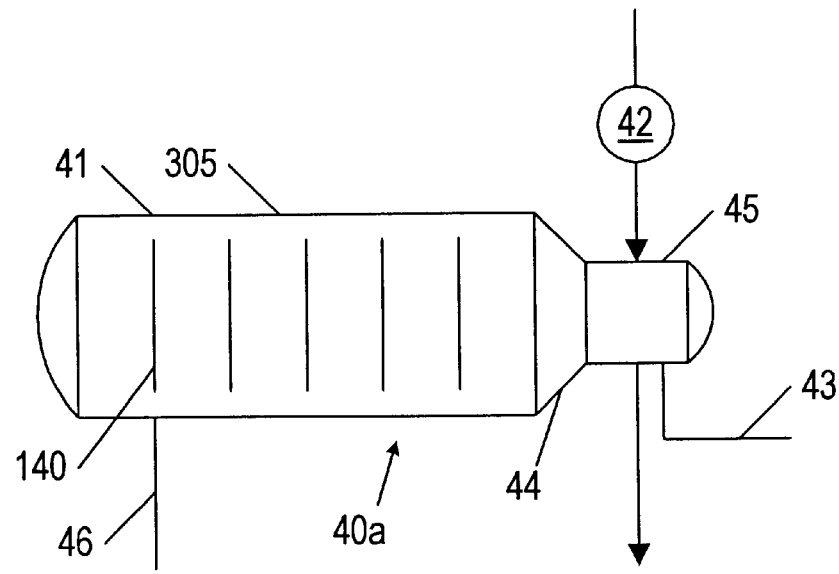
FIG. 1C (a–b) depicts alternate embodiments of first recovery system 40.
Figure 1C:
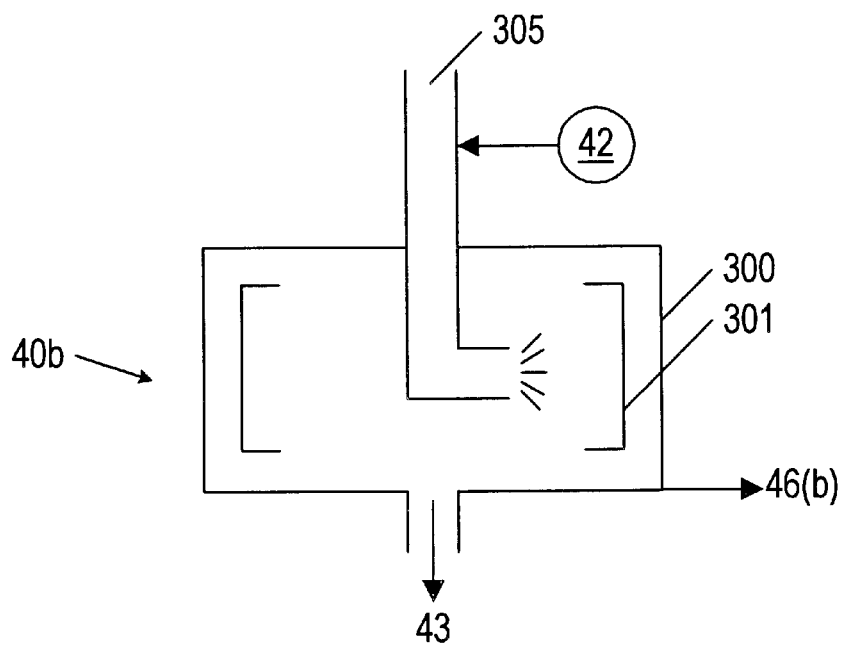

As shown in FIG. 1C (*b*), a vertical centrifugal filter 300 may include a perforated basket 301 upon which the crystals in line 305 (i.e., from the crystallizer) are filtered from the mother liquor. Wash and mother liquor exit filter 300 via line 46(*b*), which is fed to column 60.

First recovery system 40 alternatively includes at least one screen bowl centrifuge 41 (see FIG. 1C (*a*)). Screen bowl centrifuge 41 preferably contains flights 180 that are adapted to direct adduct solids up beach section 44 and into screen section 45. Liquid may be directed toward the end of centrifuge 41 opposite screen section 45, upon which it may be directed to drying tower 60 through conduit 46. Wash system 42 may be employed to wash the solids recovered in screen bowl centrifuge 41. The wash preferably occurs in screen section 45 of centrifuge 41 with clean phenol serving as the wash fluid.

The recovered adduct solids are preferably crystals with a mean crystal width exceeding about 180 microns, and a mean length to width ratio below about 5:1. The recovered cake of the crystals preferably has a free liquor content of less than 6%. The crystals may in some embodiments have a rhombic shape.

In an embodiment, the recovered adduct is directed through conduit 43 from the solid-liquid separator 41 to mixing system 50, where water is mixed with the adduct solid to form an adduct solution with a melting point less than 150° C. The melting point of the adduct solution is preferably between about 60° C. and 120° C., and more preferably between 60° C. and 80° C. The mixing system preferably includes vessel 51 and agitator 52. In an embodiment, the mixing system also includes a heating system adapted to heat water to a temperature of about 150° C. or less. Water is preferably directed into vessel 51 from water system 59 through conduit 53 preferably at a temperature below about 150° C., more preferably between about 60° C. and 150° C., and more preferably still between about 60° C. and about 90° C. The residence time of the materials within vessel 51 may preferably be less than 5 minutes, and more preferably less than 1 minute. The adduct solution is preferably mixed and continuously directed to column 70 through conduit 54.

Control system 150 may be used to regulate the rate at which the adduct solution or melt is directed to column 70. In each of the following embodiments, control system 150 is adapted to send and receive signals from flow elements 151, 152, and 153, water system 59, pump 55, and heating system 57.

Flow elements 151, 152, 153 are each adapted to sense conditions of a stream including temperature, pressure, and/or flow rate. Element 151 includes a flow control valve to adjust the amount of water added to vessel 51. Element 153 includes a flow control valve to adjust the rate of adduct solution leaving vessel 51. In an embodiment, elements 151 and 153 each relay a signal to system 150 indicating the rate of flow through the given element. System 150 determines the rate of adduct solid directed into vessel 51 from the relayed signals and controls the flow control valve of element 151 to direct a specified amount of water to vessel 51.

In an embodiment, element 152 relays a signal to system 150 indicating the flow properties (e.g., flowrate, temperature, pressure, composition) of the effluent of system 20 that enters centrifuge 41. System 150 determines a selected amount of water to be directed into vessel 51 from the relayed signal and controls the flow control valve of element 151 to direct a specified amount of water to vessel 51.

In another embodiment, system 150 regulates the temperature of the water added through conduit 53 by sending signals to a heating system comprised in water system 59. The heating system of water system 59 adjusts the temperature of the water to a selected temperature below about 150° C., and more preferably between about 60° C. and about 90° C. The signal sent from system 150 to the heating system within system 59 is determined by signals received by system 150 from any of elements 151, 152, or 153.

In another embodiment, system 150 controls the pumping rate of pump 55 as a function of the signals received from the above-mentioned elements.

Numerous additional control schemes employing the above-mentioned elements and control system may be used.

According to an embodiment, the adduct solution is treated in an ion-exchange (e.g., anionic) system 58. System 58 tends to reduce and/or eliminate the presence of species such as trace acids and chlorides in the adduct solution that catalyze the decomposition of bisphenol A. In an embodiment, the adduct solution is at a temperature of between about 60° C. and about 65° C. as it is passed through anionic exchange system 58 to remove acidic species and chlorides from the adduct solution. Conventional methods are not adapted to treat the adduct solution in the manner of the present invention to remove acidic species and chlorides. An anionic exchange resin suited for such a purpose will lose its stability above about 65° C.

Solids that enter anion exchange system 58 will tend to plug the system. The addition of water to the adduct solid or adduct solution lowers the melt point of the resulting adduct solution allowing it to pass through system 58 substantially as a melt at a temperature of less than about 65° C. Anionic exchange system 58 is preferably located upstream of column 70.

In an embodiment, injection system 69 (shown in FIG. 4) is used to add heated water and/or pressurizing steam to the adduct solution prior to its entrance into column 70, thereby preferably increasing the temperature of the adduct solution to above the temperature at which the adduct solution would flash under the pressure of column 70. The steam preferably is at a temperature between about 135° C. and about 145° C. It may be necessary to add the steam at a temperature above 160° C. Steam at higher temperatures (e.g. above about 150° C.) can be added to the adduct solution without significant decomposition of bisphenol A if the number of moles of phenol is at least equal to the number of moles of bisphenol A in the adduct solution. If the number of moles of bisphenol A present is greater than the number of moles of phenol present, steam at higher temperatures (e.g. above about 150° C.) can be added to the adduct solution without significant decomposition of bisphenol A if mixing allows the temperature of the pressurized adduct solution to rapidly reach a temperature below about 150° C. The pressurizing steam increases the temperature of the adduct solution and/or provides sufficient pressure to allow entrance of the adduct solution into column 70.

In an embodiment, pump 55 pressurizes the adduct solution and an eductor mixer is used to direct steam from system 69 into the pressurized adduct solution. In another embodiment, the steam is saturated steam at a pressure of between about 50 psia and about 155 psia.

In an embodiment, heat exchanger 56 is used to raise the temperature of the adduct solution to about 135° C. prior to its entrance into column 70. System 69 need not be employed in combination with exchanger 56 if it is preferred to reduce the amount of water entering column 70. Pump 55 may be used to pressurize the adduct solution prior to its entrance into column 70.

In an embodiment, vessel 51 contains adduct heating system 57 to melt the adduct solids without the addition of water. Adduct heating system 57 may include external coils or other heating devices. Adduct heating system 57 is adapted to heat the adduct solids to a temperature of below 150° C., and the solids are preferably heated to about 135° C. The resulting adduct melt is directed through conduit 54 to column 70, and steam system 69 is preferably used to inject a selected amount of heated water or pressuring steam into the adduct melt prior to its entrance into column 70. In this embodiment, the total quantity of water introduced into column 70 is decreased, thereby reducing the amount of process water that must be treated. Reducing the quantity of water introduced into column 70 with the adduct solution may increase the energy that must be added to column 70 for the required removal of phenol. In an embodiment, adduct heating system 57 is used in conjunction with the method of adding of water through conduit 53 to form an adduct solution.

Figure 4:
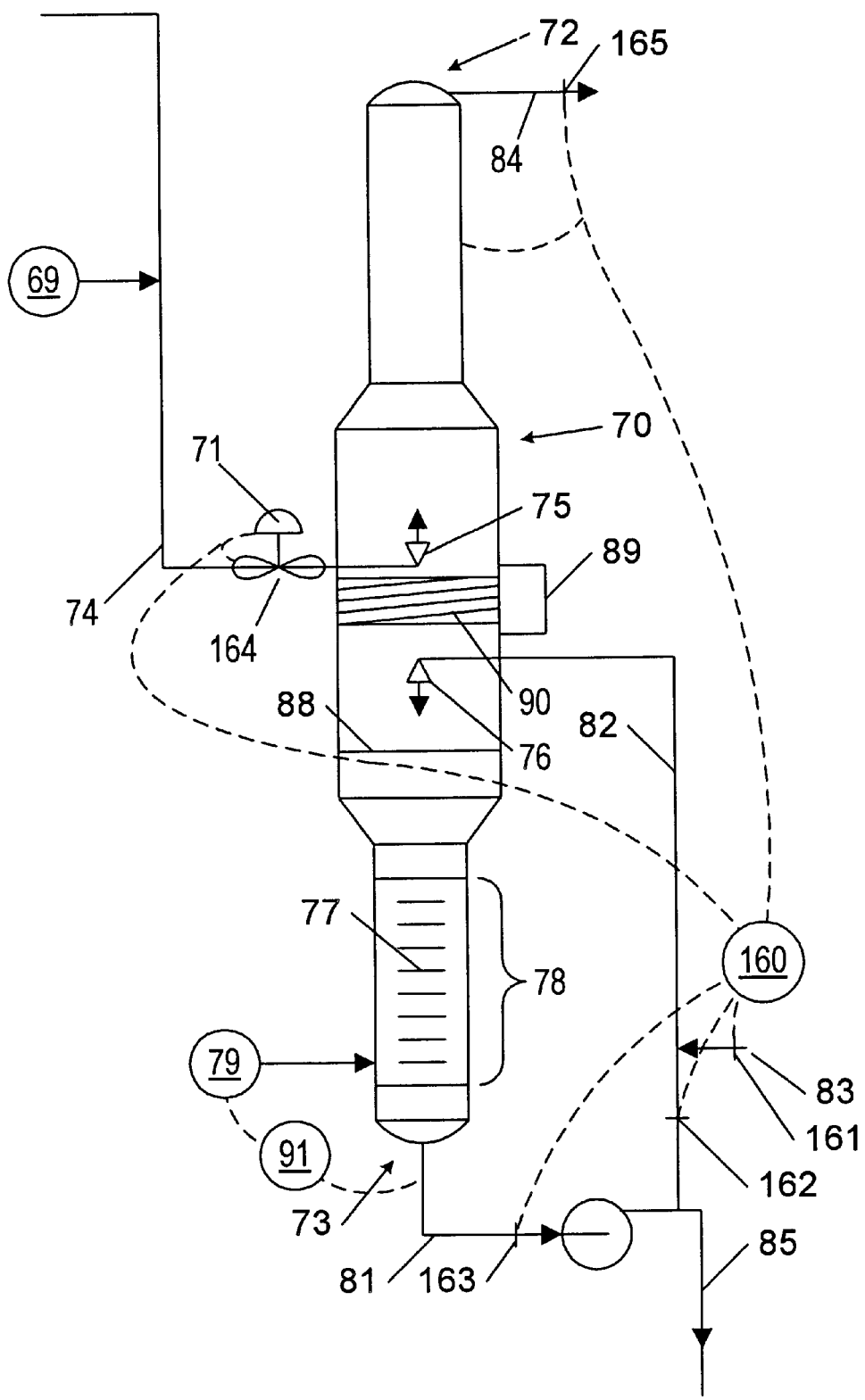
FIG. 4 is a schematic diagram of an embodiment of a column.

Referring to FIG. 4, the pressurized adduct solution is preferably at a temperature of about 135° C. as it is fed into column 70 through control valve 71. Column 70 includes overhead outlet 72 near the top of the column, bottoms outlet 73 near the bottom of the column, and feed inlet 74 between the overhead and bottoms outlets. The adduct solution preferably contains a suitable amount of water to allow the removal of phenol via steam stripping at a temperature well below 150° C. in a column having a pressure of at least atmospheric pressure. Some practitioners use vacuum systems to reduce the pressure within a column to below atmospheric pressure, thereby lowering the required column temperature. The use of a vacuum system, however, does not allow the column temperature to be reduced below 157° C. since bisphenol A would tend to freeze in the column. In contrast, column 70 is preferably operated at a pressure of at least atmospheric pressure to prevent seepage of air into the process stream. It is preferred to minimize the amount of oxygen in the system to minimize the formation of color bodies. In a preferred embodiment, column 70 is operated at the pressure which causes the adduct solution entering column 70 to begin boiling at about 110° C.

At least a portion of the adduct solution preferably flashes due to the pressure drop experienced across control valve 71. In one embodiment, first distributor 75 is employed to feed the adduct solution to column 70 in a direction upward and parallel to the wall of the column to prevent the adduct solution from contacting the column wall and forming solids on the column wall. In another embodiment, the column wall is heated using heating system 89 to prevent at least some of any adduct solution that contacts the column wall from forming solids on the wall. The heating system may include coil 90 or various other heating devices. Coil 90 may be adapted to contain steam or other heating media. Coil 90 may be placed along any segment of the column wall. The wall is preferably heated to a temperature of between about 110° C. and 150° C., and more preferably between about 130° C. and about 135° C. First distributor 75 and heating system 89 may be used in conjunction with each other. In an embodiment, heating system 89 includes coil 90 along part or all of the length of column 70, and steam is passed through the coil to heat the column wall.

In an embodiment, second distributor 76 is employed to distribute fluid toward the bottom of column 70. The lower portion 78 of column 70 preferably contains trays, rings, or packing 77, and heated water injection system 79 may be used to inject heated water into column 70 through an injection port near the bottom of the column. In an embodiment, the heated water is in the form of superheated steam. The injection of heated water or steam near the bottom of column 70 may facilitate the removal of phenol remaining in the liquid phase. In an embodiment, control system 91 may be used to monitor the temperature or phenol content of bottoms stream 81 and regulate the addition of heated water or steam into column 70 via system 79 as a function of the temperature or phenol content. The bottom of column 70 is preferably at a temperature of between 100° C. and 115° C., and is more preferably at a temperature of 110° C. Some solids may be allowed to travel through trays, rings, or packing 77 within lower portion 78 of column 70, however in an embodiment, distribution tray 88 is employed to inhibit solids from entering the lower portion 78 of the column. Distribution tray 88 preferably prevents a sufficient amount of solids from entering lower portion 78 to prevent significant plugging within packing 77. In one embodiment, packing 77 may extend from lower portion 78 up to distribution tray 88.

Bottoms stream 81 is drawn from at or near the bottom of column 70 and preferably includes less than about 1 weight percent phenol, and more preferably includes less than about 0.5 weight percent phenol. Bottoms stream 81 preferably includes about 80–85 weight percent bisphenol A and about 15–20 weight percent water. If the water content in the stream rises above about 15 weight percent, two liquid phases will tend to form: an organic phase including about 80–85 weight percent bisphenol A and about 15–20 weight percent water, and an aqueous phase including water and a small amount of soluble bisphenol A. Bottoms stream 81 preferably includes slightly above 15 weight percent water such that an emulsion is formed and excess water is present to dissolve solids. A first portion 82 of bottoms stream 81 is preferably recycled back into column 70, preferably at a point above tray 88 and below first distributor 75 to prevent the absorption of vapor that contains phenol into stream 81. The recycled bottoms portion 82 is preferably directed toward tray 88 through second distributor 76. The recycled bottoms portion serves to wash and dissolve at least a portion of any bisphenol A solids formed in column 70. In an embodiment, water or steam is added to recycled bottoms portion 82 through conduit 83 to enhance the dissolution of the solids, although the addition of such water is not anticipated to be necessary. Column overhead stream 84 includes phenol and water, and is directed to drying tower 60.

Control system 160 is adapted to send and receive signals from flow elements 161, 162, 163, 164, and 165. Each of these flow elements is adapted to sense conditions of a stream including temperature, pressure and/or flowrate. Control system 160 is adapted to sense column conditions including pressure and temperatures at a plurality of sites along the length of the column including at tray 88 and at a feed tray in the column. Some or all of the above-mentioned flow elements preferably contains a flow control valve. In an embodiment, an overhead stream flows from at or near the top of the column into a partial condenser, and a portion of the overhead stream is recycled back into the column to maintain a selected pressure within the column. The amount of the portion recycled is preferably regulated by system 160. In an embodiment, control system 160 regulates the rate of water added to bottoms recycle stream 82 through element 161 as a function of the flow rate of bottoms recycle stream 82 through element 162. In another embodiment, a sample of bottoms stream 81 to determine its composition is taken at element 163, and controller 160 regulates the amount of bottoms stream 81 that is directed through element 162 and the amount of water (if any) that is directed through element 161. Numerous other control schemes employing the above-mentioned elements may be used.

Drying tower 60 is adapted to separate acetone and water from bisphenol, impurities, and phenol. Overhead stream 61 includes acetone and water and is directed to a system for acetone recovery. Bottoms stream 62 contains phenol, bisphenol and impurities, and is directed to a system to recover clean phenol to be used as a phenol wash in wash system 42.

A second portion 85 of column bottoms stream 81 is preferably directed to second solidification system 100. In an embodiment, water is added to second portion 85 via conduit 86 to form feed stream 87 including about 45–55 weight percent water, about 45–55 weight percent bisphenol A, and less than about 1 weight percent phenol. Feed stream 87 includes an organic phase and an aqueous phase and may contain an overall water content up to about 75 weight percent. The organic phase includes about 80–85 weight percent bisphenol A and about 15–20 weight percent water, and the aqueous phase includes water and a small quantity of soluble bisphenol A. In an embodiment, second solidification system 100 includes a crystallizer 103 that contains agitator 104. In an alternate embodiment, second solidification system 100 includes a Svenson draft-tube baffled crystallizer, or a sufficiently agitated vessel. FIG. 1B (*a*) depicts a forced circulation crystallizer 103(*a*). FIG. 1B (*b*) depicts a draft-tube crystallizer 103(*b*). FIG. 1B (*c*) depicts a Svenson draft-tube baffled crystallizer 103(*c*).

In an embodiment, crystallizer 103 is operated at a pressure below atmospheric pressure such that the boiling point of water is maintained at a temperature ranging from about 80° C. to 120° C., and more preferably from about 94° C. to about 98° C. It may be appreciated that, in general, as temperature increases, then purity increases but yield declines. As such, temperature ranges such as 90–92° C., 92–94° C., 94–96° C., and/or 96–98° C. may be employed. The absolute pressure is preferably maintained at about 500–700 torr, and more preferably at about 600 torr. The vacuum may be achieved by vacuum system 101, which may include jet ejectors or a vacuum pump. Second solidification system 100 may contain cooler 102 to condense a portion of the vapor entering cooler 102 via line 201 (and returning to crystallizer 103 via line 202) that is boiled in crystallizer 103. Solids may be deposited on the walls of crystallizer 103 due to the boiling of the fluid within crystallizer 103. In an embodiment, water is added to system 103 from water system 105 to minimize the evaporative cooling required, thereby inhibiting excessive deposits from forming on the crystallizer wall. In an embodiment, water system 105 includes a water dispersing system (e.g., sprinkler, sprayer, distributor) to introduce water into system 103 (e.g., drop water onto surface). It is believed that dispersing water in this manner enhances the formation and/or development of solids (e.g., crystals) in system 103.

In an embodiment, second portion 85 is directed to second solidification system 100 without the addition of water through conduit 86. Water system 105 is preferably used to add water at a select temperature directly to crystallizer 103 to maintain the temperature within crystallizer 103 between about 80° C. and 120° C., and more preferably between about 90° C. and 100° C. and to maintain an overall composition within crystallizer 103 that includes about 45–55 weight percent water and about 45–55 weight percent bisphenol A. Water is heated or cooled to a selected temperature using exchanger 107. This embodiment does not require the use of vacuum system 101 or cooler 102, since the temperature of crystallizer 103 is maintained through the addition of water at a selected temperature. Thus the entry of air into the process as a result of a vacuum system is avoided. In an embodiment, vacuum system 101 and cooler 102 are used in conjunction with the addition of water from water system 105 at a selected temperature.

In an embodiment, effluent 106 from second solidification system 100 is directed to second recovery system 110 where the high purity bisphenol A product is recovered. In an embodiment, the second recovery system contains at least one pusher centrifuge 111 and a wash system 112 for washing solids recovered in centrifuge 111. Pusher centrifuge 111 preferably contains more than one stage and is adapted to accept wash fluid from wash system 112 at a plurality of sites. The recovered solids are preferably washed with water. Dryer 113 accepts recovered solids through conduit 122 and further reduces the water content of the solids. Dryer 113 may be a fluid bed dryer 113 B or a contact dryer 113 A (see items I and II in FIG. 1A). Fluid bed dryer 113B may be vibrating and may include a perforated, conveying tray 115D. Various other dryers such as rotating tray, batch, or inclined dryers may be used. Nitrogen gas is preferably added to contact dryer 113 to reduce the partial pressure of water and facilitate its removal from the recovered solids, while steam preferably serves as the heating agent and is added to dryer 113 A using steam system 114. The water content of the recovered solids is preferably reduced to below 1500 ppm. Additional drying systems may be used downstream of dryer 113 to further reduce the water content of the recovered solids. If fluid bed dryer 113B is used, then a heating fluid such as hot nitrogen may be introduced via line 114B into distribution plenum 115B. Moist heating fluid may exit dryer 113B via conduit 115C.

The bisphenol A product is collected in hopper 120. The recovered bisphenol A product includes at least about 99 weight percent bisphenol A, more preferably at least about 99.7 weight percent bisphenol A, and more preferably still at least about 99.9 weight percent bisphenol A. In a preferred embodiment, bisphenol A in the product has only been exposed to a temperature in excess of 150° C. while phenol was in molar excess of bisphenol A. In a more preferred embodiment, the greatest process temperature to which the bisphenol A in the product has been exposed is less than 150° C.

Plant Experiments

Experiments were conducted in a BPA plant south of Bombay, India ("the Indian plant" or "the Indian process"). As operated in 1994–95, the Indian process included a reaction zone utilizing cation exchange resin followed by a crystallization zone that formed adduct crystals. The adduct crystals included a one-to-one molar ratio of phenol and BPA. The adduct crystals were recovered from the mother liquor, redissolved in clean phenol and re-crystallized in a second, identical crystallization zone. The re-crystallized adduct crystals were again recovered and melted, and the phenol was removed by vaporization and steam stripping after which the final product BPA was solidified on a drum flaker. The primary and secondary mother liquors were both recycled to the reaction zone after being treated and/or used in various associated functions of the process. Water of reaction was purged from the system after removal of small quantities of contaminating phenol. Raw material was recovered from a purge stream of concentrated heavy impurities and residual BPA by treatment in a catalytic cracking system. After such treatment polymers and uncleavable heavy impurities were purged from the system. Fresh acetone and phenol were added to the system to compensate for the quantities of such materials that were consumed in the formation of BPA and/or lost as waste.

In the Indian process acetone and phenol are reacted in two sequential reactors. The reactor effluent flows directly to the primary crystallizer system after which the adduct crystals are separated from the mother liquor and are re-dissolved in cleaner phenol for recrystallization in the secondary crystallizer system. The adduct crystals from the secondary system are separated from the cleaner secondary mother liquor and are then melted. The majority of the phenol in the adduct crystal melt is vaporized from the higher boiling BPA in a wiped film evaporator leaving a BPA melt containing about 1–2% residual phenol. This residual phenol is removed in a packed tower by stripping with superheated steam. The BPA melt is solidified on a drum flaker and immediately bagged and stored in a warehouse.

The mother liquor from the primary system contains water, acetone, impurities and residual BPA. This mother liquor is passed through preheaters into a flash chamber where the water, acetone and a portion of the phenol is flashed to a vapor. This vapor is fed to a distillation column for separating the water and acetone from the lower vapor pressure phenol. The bottoms stream from the flash chamber includes a concentration of impurities and residual BPA in a phenol carrier. From this stream, a small purge is taken to a catalytic decomposition zone where the phenol is distilled overhead and the BPA and impurities are cleaved at high temperature to form phenol and isopropenyl phenol. Phenol is recovered as raw material and recycled to the reaction zone. Uncleavable "heavies" and polymers are purged from the system as "tars." The balance of the flash pot bottoms stream is recycled to the reaction zone.

The phenol in the flash pot vapor is condensed in the drying column and a portion is eventually used as the "cleaner phenol" to redissolve the adduct crystals from the primary crystallization system, and to generate the solution feed to the secondary crystallization zone. The balance of the phenol is recycled to the reaction zone. The acetone, water and a small amount of phenol vapor are fed directly into a second distillation column where the acetone is recovered as distillate, and the water and a small amount of phenol are removed from the column bottoms. The phenol is absorbed from the water in alternating beds of absorbent resin beads. The water is sent to a bio-treatment pond and discharged to a public waterway. The absorbed phenol is removed from the absorber beds by washing with a portion of the recovered acetone. These acetone and phenol streams are sent back to the drying tower to separate the acetone and water. The balance of the acetone that was not used to wash the absorber beds is recycled to the reactors with additional acetone to replace the acetone used in the formation of the BPA.

The mother liquor from the secondary crystallization zone is used to wash the crystals from the primary crystallization zone. This mother liquor is combined with the primary mother liquor feed to the flash chamber.

Make-up phenol to replace the phenol consumed in the formation of the BPA is mixed with the phenol distillate from the adduct crystal melt processed through the wiped film evaporator. This mixture is used to wash the adduct crystals from the secondary crystallization zone.

The water and phenol from the stream stripping tower is condensed and fed to the drying tower.

The Indian process uses 160 cubic meters, as received volume, of unpromoted cation exchange resin catalyst to produce 5000 metric tons/yr of BPA. The Indian plant reactors are operated in series in an upflow mode at a design feed rate of about 5 metric tons/hour with circulation through an external cooler at a circulation rate to feed rate ratio of about 5:1, thus limiting temperature rise to about 1–2 degrees centigrade. The temperature rises from about 70 to about 71–72 degrees Celsius.

The reactor feed in the Indian process contains 13–15% BPA (design is 10%) and 18–20% total impurities (design is about 17%). The reactor effluent contains about 28–29% BPA (design is about 25%) and about 18–20% total impurities (design is about 17%).

The Indian plant reactor feed and effluent streams are wet at 0.8–1.0% and about 1.9 to 2.0% water, respectively.

In the Indian process the total acetone sent to the reactor zone based on net reactor feed is around 5.5–6 percent. This acetone is split with about ⅓ being fed to the first reactor and about ⅔ being fed to the second reactor (the design is almost exactly the opposite). There is an increase of about 14 to 15% BPA across the reactors which consumes about 59–65% of the acetone fed, leaving about 2–2.5% acetone in the reactor effluent.

The reactor effluent in the Indian process is sent directly to the primary crystallization zone. The primary crystallization zone of the Indian process includes three sequential stirred, dished-head pressure vessels, each of which contains an internal cooling coil and an external "limpit" or half-pipe jacket (i.e., a jacket having a cross-sectional shape corresponding to at least part of a semi-circle). FIG. 2 is representative of these vessels. Each vessel contains two sets of agitator blades on a single shaft, one about midway down the shaft and the other slightly above the bottom of the vessel. The agitator blades are all flat, sharp edged plates set at an angle of 45 degrees.

There is no cooling of the reactor effluent prior to the first crystallization vessel. In the first crystallizer the process is cooled from about 70–71 degrees C. to about 55 degrees C., in the second crystallizer the process is cooled to about 45 degrees C. and the third reduces the process temperature to about 40 degrees C. Due to line plugging problems caused by poor temperature control (poor tracing installation and poor maintenance), the process is reheated to a temperature of about 50–52 degrees to avoid the effects of cold spots on the feed line to the solids/liquid separation unit.

In addition to the details listed above, the primary crystallization zone of the Indian system includes two standard high speed centrifugal pumps and three recycle streams that insure that the entire crystal slurry will be repeatedly subjected to the turbulence of the sharp edged agitators and the stresses within each of the centrifugal pumps, and to insure that the initial crystallizer vessel is continuously flooded with crystals from the last crystallizer vessel.

The above description of the primary crystallization zone is applicable to the secondary crystallization zone. Therefore the entire system contains six serially arranged crystallizers with sharp edged flat plate agitators, four centrifugal pumps, and six recycle streams all of which seem contrary to accepted good practice for promotion of good crystal growth. Additionally, the stream levels and temperatures of all of the units fluctuated frequently.

Figure 7:
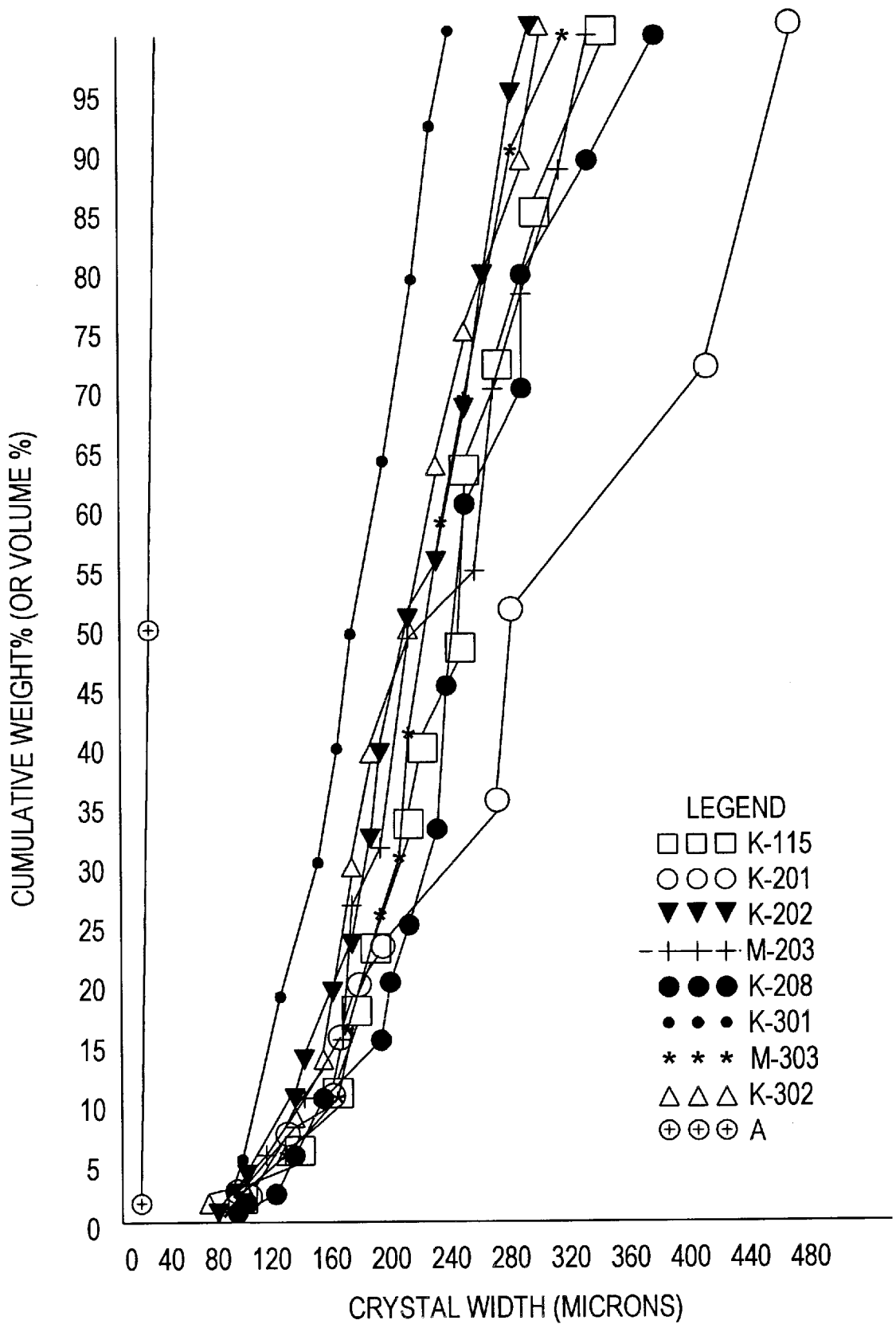
FIG. 7 is a plot of cumulative volume/weight for various solids (crystals) made in a plant in India.

As would be expected with such a system, the adduct crystal size distribution was extremely small with minor axes ranging from about 6 microns to about 30 microns and a mean minor axis (width) on a cumulative volume basis of about 18 microns. See curve A on FIG. 7. The x-axis of FIG. 7 depicts crystal width (in microns) and the y-axis depicts the cumulative volume for a given sample, in cubic microns. Cumulative volume was calculated by the equation: Cumulative Volume=width×width×length. Since the density of all of the crystals in a given sample is approximately equal, the mean width calculated on a cumulative volume basis would be equal to the mean width calculated on a cumulative weight basis. The curves on FIG. 7 were drawn by hand, with the data points being collected from the Indian plant.

In the Indian system the adduct crystals from the primary crystallization zone are recovered in a centrifugal filter followed by redissolving in phenol. This solution is then passed to the secondary crystallization zone, which is identical to the primary crystallization zone, where the product is recrystallized as phenol/bisphenol adduct crystals. These crystals are recovered and washed in a second centrifugal filter and the crystals are passed on to a melt vessel where they are melted at about 135–140 degrees C. The melt is pumped to a wiped film evaporator where the majority of the phenol is removed at about 180 degrees C. and around 30 to 50 mm Hg. absolute pressure. The product from this unit contains 1 to 2% phenol which is removed in a subsequent tower by stripping with superheated steam.

Thermal and/or catalytic cracking (decomposition) of the BPA and impurities begins in the wiped film evaporator and continues throughout the following system until solidification.

The final product melt is solidified on a drum flaker from which the flake goes directly to a bagging hopper and is bagged as the flake is generated.

The flaked product has an assay of about 99.7 to 99.8% BPA with about 0.2 to 0.3% total impurities. The ortho para isomer of BPA is low in this product. Phenol and reaction products of decomposition seem to constitute the majority of the impurities and, in December, 1994, product color of 40–50 APHA was the overriding problem. "APHA" refers to a color scale promulgated by the American Public Health Association for water. APHA color measurements were made using a Klett-Summersett calorimeter, using filter no. 42.

The Indian product had been judged to be unacceptable as a raw material for production of polycarbonate resins by General Electric Plastics, a major global producer of polycarbonate resins, even when the product color was 15 APHA.

The particles from the Indian plant had sizes and shapes ("habits") that were considered particularly poor. Prior technical experts took the position that Indian's centrifugal transfer pumps were grinding the crystals to small particles. These experts suggested replacing the centrifugal pumps with some type of gentle pump designed for slurries (e.g., a diaphragm pump). Other suspected causes of crystal grinding included the sharp edge flat plate agitators, and the control valves controlling the flow of slurry. The Indian design appeared to be particularly poorly suited for controlled crystal growth.

Pursuant to conventional wisdom, certain improvements were attempted. Diaphragm pumps were installed in the Indian plant, and a frequency converter was installed to reduce agitator speeds. In addition, attempts were made to modulate the swinging levels and temperatures somewhat, and to stop or reduce the recycle flows.

Crystal samples were taken after the above improvements were made and the system had reached steady state. These samples indicated essentially no change in crystal size distribution. Worse still, fouling of the cooling surfaces had increased significantly due to the reduced agitator speeds. The operational interval between "remelts" decreased dramatically and production began to decrease. Clearly the "conventional wisdom" did not work for the Indian plant.

At this point the frequency converter was used to increase the agitator speed above original design. The operating time between remelts increased, indicating a significant increase in heat transfer. Within a day the centrifuge performance had improved and production was increased by around 20% from about 13–14 metric tons per day to 16–17 metric tons per day. The original design capacity for the Indian plant was 15 metric tons per day.

Adduct crystals were again sampled from selected points within the crystallizer trains. Analysis indicated that the crystal size had increased significantly, appearing visually to be at least 3–5 times the size of the crystals from the original sample in which the crystal widths had ranged from 6 to 30 microns.

After some time the agitator speeds were increased again to almost the maximum allowed by the motor power. Again heat transfer increased as evidenced by another increase in operating time between necessary remelts, followed by another improvement in centrifuge operation. Production increased to 19–20 tons per day for a total increase of 40–45% above the starting point and 27–33% above design.

At this point adduct crystals were sampled from all of the 6 crystallizers and the two surge pots that receive the effluent from each crystallizer train, and from which the centrifuges are fed. The samples showed a nearly complete absence of any particles that could be considered as 'fines'. There were no particles with widths or minor axis under 60 microns from any of the units sampled and the cumulative weight of particles with minor axis under 80 microns totaled less than 1%. The mean width of the smallest sampling was 190 microns on a cumulative weight basis, and the mean width of the largest sampling was 300 microns. The mean widths of the other six samplings fell between those two with an average mean width of between 220 and 240 microns.

The most surprising data was the major axis-to-minor axis ratio (i.e., the length to width ratio). The average of the ratios for all samples was 1.8 to 2.0 indicating a drastic altering of the crystal shape to shorter, more robust crystals.

Samples of the crystal cake from the centrifuge receiving the slurry from the primary crystallizer train showed total phenol analysis of 29 to 30%, down from 35 to 40% in the earlier samples (absolutely dry crystals should be 29.2% phenol). Samples of crystal cake from the centrifuge receiving the slurry from the secondary crystallizer train showed somewhat higher phenol content of 30 to 33%. This higher content was surprising in that the viscosity of the primary mother liquor should have been significantly higher than the viscosity of the secondary mother liquor because of the much higher content of impurities (at around 22 to 25%) versus no more than about 1% impurities in the secondary mother liquor.

The product color had improved considerably after some operating changes to the flash system prior to the drying tower. Primary mother liquor having high impurities and high color is processed through this system. The mother liquor is fed into the flash system and the overhead vapor is fed to the drying tower. This overhead was supposed to be clean phenol, acetone, and water vapor but color bodies and heavies were found to be flowing overhead also. The bottoms from the drying tower are eventually used as the solvent for the adduct crystals from the primary system, thereby making the solution feed to the secondary system. Therefore color bodies that were carried over with the flash vapor into the drying tower would eventually end up in the secondary mother liquor and contribute color to the product in direct proportion to the amount of mother liquor left in the cake.

Three other sources of color bodies and impurities had been found and mitigated prior to the work with the crystallizers. One was the fresh phenol as it was brought in by tank truck. It was found to have high color and color body precursors with a vapor pressure very close to phenol, thereby preventing separation from phenol by distillation. A cation bed was installed to react the impurity with phenol to form a compound having a low vapor pressure which would allow separation of the impurity as a heavy by distilling off the phenol. The installation and startup of this bed was completed prior to the crystallizer work.

The second source of color bodies was from corrosion, iron and product decomposition that was a result of improper treatment of the steam boiler feed water, and which was resulting in about 30 ppm chlorides in the steam used to strip the residual phenol from the BPA prior to flaking. Chlorides were concentrating in the system causing stress cracking corrosion of the stainless steel drying tower and catalyzing decomposition of BPA at high temperatures. The decomposition products were reacting to color body precursors and color bodies.

The third source of impurities and color bodies was found to be the catalytic cracking system for recovering raw material value from the heavy impurities that were purged from the process. This purge was taken from the bottoms stream from the system mentioned earlier for flashing the primary mother liquor prior to the drying tower. The purpose of the flash system, in addition to supplying a clean stream of vapor to the drying tower, was to generate a stream containing concentrated impurities from which to draw the purge to the catalytic cracking system. It was found that the catalytic cracking system was causing increased losses in the form of heavies generated from polymerization of impurities. Color body precursors, color bodies, and impurities were being recycled to the system with the recovered raw material, causing an increase in impurity concentration throughout the process and tremendously increasing the color of all of the process streams. This operation was improved to reduce the recycling of impurities and color bodies to the main process streams. This operation was even shutdown completely for several months, which contributed to the reduction of the color of the process streams prior to the crystal size distribution improvement.

The combined effect of the improvements described above had reduced the product color to about 20 APHA from the earlier high of 40 to 50 APHA.

With the larger crystal size distribution and the improved shape, the deliquoring of the cake in both the primary and secondary centrifuges improved to the point that the cake colors were actually lower than the color of the phenol streams used for wash. For example, the phenol used to wash the cake in the primary centrifuge was eventually reduced to a color of about 20 APHA but the cake discharged from the unit had a color of 10 APHA, and the cake discharged from the secondary centrifuge had a color of 5 APHA even when it was washed with phenol with a color of 10 to 15 APHA.

It is believed that the BPA/phenol adduct crystals generated as described herein have an unprecedented combination of size and shape. These crystals form a cake with desirable deliquoring characteristics and wash efficiencies.

An unusual characteristic of the discoveries outlined herein is that the operational change (turbulence) that seems to have the major controlling influence on improving the crystal shape also has a very favorable effect on the heat transfer and, therefore, the production capacity of the crystallization system. The same parameter that causes the crystal to assume a favorable shape has a favorable impact on the system capacity.

To change the crystal shape from long and slender to short and stubby, it seems that relatively high turbulence is required. It is believe that the intensity of the turbulence, however, must be short of that required to generate spontaneous or secondary nucleation. It is difficult to predict the exact optimum turbulence for any given system because of the effects of boundary shapes, the characteristics of different agitators or pump impellers, process stream compositions and temperature, the degree of supersaturation, the viscosity of the crystallization medium, effects of crystal density, etc. The most efficient approach appears to be to empirically determine the relationship between the ratio of the crystal major axis to the minor axis relative to agitation or circulation. To make this determination, crystal size distribution data are taken for a given set of conditions and an average of the major-to-minor-axis-ratios is calculated for the data set. The agitator speed or circulation rate is then increased and the system resampled after reaching equilibrium. These steps are repeated as long as the ratio of the major-to-minor axis continues to decrease and secondary and/or spontaneous nucleation is not encountered. Crystallizer unit capacity will tend to increase with each increase in agitation or circulation.

In some systems additional steps can be taken to improve the crystal size distribution as well as to improve the shape of the crystals. These include retrofitting the flow conduits to allow the reactor effluent to go directly to the crystallization zone instead of removing the water of reaction and residual acetone prior to crystallization. This change has the positive effect of reducing the viscosity, which should increase heat transfer at lower velocities and allow optimization of turbulence at reduced power consumption (in addition to improving crystal growth and size distribution). An additional method of maximizing crystal size distribution is to install a system for partial or total reduction/destruction of fines.

Incorporation of these additional approaches will increase the crystal size distribution, however such approaches also may have some negative side effects. The increase in water concentration in the crystallization zone that will be experienced if the reactor effluent is used directly as the crystallization medium will also tend to increase the solubility of BPA in the mother liquor and could have a deleterious effect on the recovery of BPA per process pass. The installation of a fines reduction and/or destruction system will tend to increase the overall heat load on the crystallizer cooling system, thereby negatively impacting crystallizer capacity.

Determination of which system or combination of systems would be optimum for any given process will require analysis of the strengths and weaknesses of the individual system.

After the improvements detailed above were made to the Indian process, samplings of the cake from the primary centrifuge showed crystals being produced with a color of 10–15 APHA, total phenol content of 30 to 33%, total impurities content of 0.13 to 0.27% from mother liquor with a color of 1500 APHA, residual bisphenol of 12 to 13% and total impurities concentration of 20 to 25% (a ratio of impurities/BPA of 1.67/1 to 1.92/1). The crystal quality described above was produced from the mother liquor described above and the crystals came from a cake that was washed with phenol having a color of 40 APHA (3 to 4 times the color of the resulting cake).

These data indicate that a small amount of impurities is within the crystal structure itself and that a system that produces crystals that form a cake with good characteristics can produce high purity product from a mother liquor with a seemingly excessively high impurity concentration. As such, with quality crystals and a good crystal processing system, closed loop operation in which the "reject" BPA stream from the secondary crystallization zone is recycled 100% to the primary crystallization zone is a viable concept. This closed loop operation is essentially the way the Indian process ran for about 3 months during a time period when the catalytic cracking system was totally shutdown. There was no detectable increase in the system of either the total mass of impurities or the average concentration of impurities during this entire time when the purge of heavy impurities from the system was zero.

After reaching equilibrium, small quantities of impurities may or may not be generated in the reaction zone of the process. In addition, a significant portion of this small quantity of impurities that may be formed in the reaction zone are very likely due to reaction of some of the decomposition products that were generated in a different area of the plant. In the Indian plant, it is believed that the catalytic decomposition section of the system was destroying raw material instead of recovering it. In addition, it is believed that this system was contaminating the main process with heavy impurities and color bodies (and maybe color body precursors) probably to a larger extent than any other single source.

An effective method of decolorizing process streams in the Indian plant included passing the stream through a "mixed" bed of cation and anion exchange resins. The bed was not actually mixed, since the anion resin was on bottom and the cation resin was on top. This treatment was found to be far more effective than treatment with either the cation or anion exchange resin alone. It worked very effectively to reduce the color of all of the process streams.

Lab reactions repeated several times indicated that maintaining contact of reaction mixtures with the catalyst after the acetone has been reacted to a very low level can result in a rapid increase in impurities formation, generally at the expense of BPA. Conditions that appear to enhance this phenomenon are relatively high concentrations of BPA and correspondingly low impurity concentrations, which tends to indicate equilibrium forces at work. This phenomenon was observed in reactions using all of the tested cation exchange resin catalysts, regardless of whether the resin was promoted or not.

It appears that a close control of acetone concentration at the end of the reaction and limitation of contact of reaction products with the catalyst after completion of the reaction may be more desirable than pushing the reaction to zero residual acetone.

Different BPA producers seem to have set different limits for impurity and BPA concentrations for good, or acceptable, crystallizer performance. Some producers try to hold BPA concentrations at no more than 20% in the crystallizer feed while others, who formerly ran the concentration at around 30%, have now reduced the limit to about 25% in the crystallizer feed. As such, it is surprising that adduct crystals having the size of the ones grown in the modified Indian system could be grown from a feed liquor containing 29% BPA and 20% impurities (these figures are based on total stream composition).

At the Indian plant the adduct crystals that were being produced prior to the modifications exhibited a size distribution on the minor axis dimension of less than about 6 microns up to about 30 microns, with a cumulative mean of about 18 microns. After the modifications the system produced the short stubby crystals described previously with a major-to-minor axis ratio of 1.8 to 2.0. Of all of the 6 crystallizer units and two following surge pots sampled, the smallest particles found measured greater than 60 microns on the minor axis and the largest particles found had a minor axis of 460 microns. The smallest cumulative weight percent mean minor axis measured for any of the 8 units was about 190 microns and the largest was about 300 microns. The average mean of all 8 units sampled was about 240 microns. These crystals were produced from the feed described above containing about 29% BPA and 20% total impurities.

As described in the process description earlier, the purification zone of the process consisted of two crystallization zones each containing three sequential crystallizers and a surge pot receiver. The crystallizers were similar in shape to those shown in FIG. 2. The surge pot, M-203, from the first three sequential crystallizers, termed "section 200," fed the first or primary solids/liquid separation system and the adduct crystals recovered from this zone were redissolved in "clean" phenol and then re-crystallized in the second three sequential crystallizers, termed "section 300."

The "section 200" units included the first crystallizer, K-115, the second crystallizer, K-201, the third crystallizer, K-202, and the surge pot receiver, M-203. The "section 300" units included the first recrystallizer, K-208, the second recrystallizer, K-301, the third recrystallizer, K-302, and the surge pot receiver, M-303. The temperature profile in both trains starts at 55 to 60 degrees C. and drops in each succeeding unit to 40 to 43 degrees C. in the last units. The lower temperatures generally correspond to the 200 section and the higher temperatures correspond to the 300 section.

Intuition would tend to suggest that one would see crystal growth and increasing size distribution as the slurry progressed through the systems, but the samples did not support this in either the 200 section or the 300 section. In the first crystallizer of section 200, K-115, the mean width of the crystals was around 245 microns, the mean width of the second crystallizer, K-201, was about 300 microns but the mean width of the third crystallizer, K-202, dropped back to 220 microns. The mean width of the sampling of the receiver pot, M-203, which had no cooling, was back up to about 245 microns (i.e., essentially the same as the first unit, K-115. The mean width for the sampling of the first of the 300 section units, K-208, turned out to be the largest of the entire 300 section at about 265 microns, with the second unit, K-301, having the smallest at about 190 microns. The mean increased slightly to about 200 microns in the third crystallizer unit, K-302, and ending at about 225 microns in the receiver pot M-303 (see the following table).

| Unit | smallest particle width (microns) | largest particle width (microns) | cumulative wt. % mean width (microns) | average major-axis-to-minor-axis ratio |
|---|---|---|---|---|
| K-115 | >80 | ~355 | ~245 | 2.3 |
| K-201 | >80 | ~460 | ~300 | 1.7 |
| K-202 | >60 | ~310 | ~220 | 1.8 |
| M-203 | >60 | ~335 | ~245 | 1.9 |
| K-208 | >80 | ~385 | ~265 | 2.0 |
| K-301 | >60 | ~250 | ~190 | 2.2 |
| K-302 | >80 | ~320 | ~215 | 2.0 |
| K-303 | >80 | ~320 | ~225 | 1.9 |

The above data do not seem to indicate any orderly progressive crystal growth as the slurry progresses through either the 200 system or the 300 system. The data also tend to indicate that impurity concentration in the feed, at least up to about 20% impurities, has little or no deleterious effect on crystal growth. These data indicate that the crystals grown from feed containing about 20% impurities and about 29% BPA (the feed to the 200 section) tended to be somewhat larger than crystals grown from feed having an impurity concentration in the range of about 1–2% and a BPA concentration of about 35% (the feed to the 300 section).

The following three embodiments represent experiments conducted at the Indian plant. The Indian plant solidification system is directed to forming adduct crystals including bisphenol A and about 30 weight percent phenol. Although the embodiments have equivalent system characteristics, each embodiment is operated in a different manner as described below. Embodiment A is the gentlest of the embodiments, having the lowest circulation rate and the greatest difference in temperature (about 15° C.) between the cooling medium and the circulated stream. Embodiment B is characterized by a greatly increased circulation rate over Embodiment A such that a level of turbulence is achieved in the circulated stream. Embodiment B has a lower temperature difference (about 5° C.) between the cooling medium and the circulated stream than does embodiment A. Embodiment C has an increased level of controlled turbulence relative to embodiment B and has a lower temperature difference (about 3° C.) between the cooling medium and stream 34 (see FIG. 2) than does embodiment B. Embodiment C further includes fines system 31 to heat a portion of the circulated stream. Selected physical properties of the solids formed in each of these embodiments fell within the ranges summarized below.

|  | Embodiment A | Embodiment B | Embodiment C |
|---|---|---|---|
| Total Impurities in Cake. (%) | unknown | 0.4%–0.5% | 0.1%–0.2% |
| Mean Crystal Width (cumulative wt % basis, microns) | 18 | 140 | 240 |
| Mean Length to Width Ratio | 3–5 | 2–3 | 1.8–2 |
| Free Liquor Content of Solids Cake (%) | 10%–11% | 3%–6% | 1%–1.5% |

The above data illustrate the significant improvement in the physical properties of formed solids that may be observed when controlled turbulence is employed. The optimum level of turbulence and exact physical properties of the formed solids for a particular system are dependent upon a number of factors as mentioned above and may vary among embodiments of the invention.

Another process that may be performed is described as follows. The adduct crystals from the primary crystallization zone are solubilized at 60 degrees by addition of water. The temperature of the mixture is brought to about 135 degrees C. and the mixture is immediately introduced into a flash chamber where most of the phenol and some of the water are removed as vapor essentially instantaneously at 100 to 110 degrees C. leaving a liquid phase consisting of water and some phenol in solution in BPA melt at 100 to 110 degrees C. The liquid phase passes downward through a distillation column wherein remaining phenol is stripped from the liquid by steam introduced at the bottom of the column.

BPA/water melt containing approximately 85% BPA and 15% water exits the bottom of the column at 100 to 110 degrees C. It is introduced to a secondary crystallization zone where the temperature is reduced to 94–98 degrees C. by addition of temperature controlled water to absorb the sensible heat and heat of crystallization or by addition of excess hot water with utilization of evaporative cooling to remove the heat (or a combination of both). Large rhombic crystals of high purity BPA may be recovered by filtration or centrifugation or the like. The crystals may be dried of the 1 to 2 percent residual moisture to yield the final product of BPA.

A collection of data relating to some of the above-mentioned systems follows.

CRYSTAL SIZE DISTRIBUTION DATA

| Crystal No. | L/w | Actual Length (L) | Actual Width (w) | $(w^2)(L)$ | Cumulative Sum of $(w^2)(L)$ | Cumulative weight % |
|---|---|---|---|---|---|---|
| K-115 | | | | | | |
| #2 | (4.3) | 499 | 115 | 6,499,275 | 19,277,747 | 2.4% |
| #1 | (3.5) | 432 | 125 | 6,728,417 | 26,006,264 | 3.3% |
| #25 | (3.6) | 518 | 144 | 10,749,442 | 36,755,706 | 4.7% |
| #33 | (3.1) | 470 | 154 | 11,098,118 | 47,753,935 | 6.1% |
| #14 | (2.5) | 403 | 163.2 | 10,738,925 | 58,492,760 | 7.4% |
| #12 | (3.1) | 528 | 173 | 15,765,996 | 74,358,751 | 9.4% |
| #16 | (2.9) | 509 | 173 | 15,192,637 | 89,451,442 | 11.4% |
| #18 | (2.2) | 384 | 173 | 11,466,179 | 101,017,721 | 12.8% |
| #24 | (2.2) | 394 | 182 | 13,094,978 | 114,112,699 | 14.5% |
| #10 | (2.8) | 518 | 182 | 17,171,482 | 131,274,180 | 16.7% |
| #5 | (2.2) | 413 | 192 | 15,217,459 | 146,401,639 | 19% |

-continued

CRYSTAL SIZE DISTRIBUTION DATA

| Crystal No. | L/w | Actual Length (L) | Actual Width (w) | (w²)(L) | Cumulative Sum of (w²)(L) | Cumulative weight % |
|---|---|---|---|---|---|---|
| #23 | (1.4) | 288 | 202 | 11,705,057 | 158,206,697 | 20% |
| #7 | (1.6) | 317 | 202 | 12,775,463 | 171,082,260 | 22% |
| #29 | (2.1) | 422 | 202 | 17,157,417 | 188,249,677 | 24% |
| #3 | (2.2) | 460 | 211 | 20,479,660 | 208,729,337 | 26% |
| #4 | (2.0) | 451 | 221 | 21,997,191 | 230,726,428 | 29% |
| #9 | (1.3) | 288 | 221 | 14,040,760 | 244 767 288 | 31% |
| #15 | (2.0) | 432 | 221 | 21,061,140 | 265,728,428 | 34% |
| #26 | (1.7) | 394 | 230 | 20,793,925 | 286,722,254 | 36% |
| #19 | (2.1) | 490 | 230 | 25,990,004 | 312,712,359 | 40% |
| #35 | (2.5) | 624 | 250 | 38,775,300 | 351,487,659 | 45% |
| #22 | (2.0) | 499 | 250 | 31,087,780 | 382,675,439 | 49% |
| #32 | (1.9) | 499 | 259 | 33,438,472 | 416,214,011 | 54% |
| #17 | (1.7) | 432 | 259 | 29,013,764 | 445,237,776 | 56% |
| #31 | (1.5) | 384 | 259 | 25,798,902 | 471,036,697 | 60% |
| #13 | (2.1) | 538 | 259 | 36,118,462 | 507,155,140 | 64% |
| #20 | (1.5) | 413 | 278 | 31,994,708 | 539,149,748 | 68% |
| #21 | (1.6) | 470 | 288 | 39,016,758 | 578,156,705 | 73% |
| #28 | (2.3) | 672 | 298 | 59,416,191 | 637,682,796 | 81% |
| #11 | (1.3) | 394 | 298 | 34,759,488 | 672,442,379 | 85% |
| #30 | (1.5) | 480 | 317 | 48,173,775 | 720,716,254 | 91% |
| #8 | (1.5) | 538 | 355 | 67,727,401 | 788,443,655 | 100% |

K-208

| #5 | 2.5 | 192 | 76.8 | 1,132,462 | 1132462 | 0.1% |
| #38 | 4.3 | 412.8 | 96.0 | 3,704,365 | 4,936,727 | 0.5% |
| #9 | 2.7 | 288 | 105.6 | 3,211,491 | 8,148,418 | 0.8% |
| #16 | 1.8 | 201.6 | 115.2 | 2,675,462 | 10,723,760 | 1.1% |
| #18 | 1.9 | 220.8 | 115.2 | 2,930,246 | 13,754,106 | 1.4% |
| #45 | 2.3 | 268.8 | 115.2 | 3,467,255 | 17,321,361 | 1.8% |
| #34 | 3.8 | 480 | 124.8 | 7,476,019 | 24,797,380 | 2.6% |
| #30 | 1.7 | 211.2 | 124.8 | 3,279,449 | 28,086,729 | 2.9% |
| #13 | 1.7 | 211.2 | 124.8 | 3,279,448 | 31,376,277 | 3.2% |
| #31 | 3.8 | 508.8 | 134.4 | 9,190,638 | 40,466,915 | 4.2% |
| #43 | 2.1 | 288 | 134.4 | 5,202,248 | 45,769,153 | 4.7% |
| #26 | 1.7 | 249.6 | 144.9 | 5,175,705 | 50,944,768 | 5.2% |
| #22 | 2.3 | 326.4 | 144.0 | 6,768,231 | 57,713,099 | 5.9% |
| #11 | 2.8 | 403.2 | 144.0 | 8,360,755 | 66,073,754 | 6.8% |
| #8 | 1.3 | 192 | 144.0 | 3,981,312 | 70,055,156 | 7.2% |
| #17 | 2.0 | 307.2 | 153.6 | 7,247,757 | 77,302,923 | 8% |
| #40 | 1.9 | 288 | 153.6 | 6,794,773 | 84,097,696 | 8.6% |
| #4 | 3.1 | 508.8 | 163.2 | 13,451,401 | 97,649,197 | 10% |
| #1 | 2.0 | 326.4 | 163.2 | 8,693,416 | 106,342,613 | 11.0% |
| #27 | 1.7 | 288 | 172.8 | 8,499,634 | 114,942,247 | 11.8% |
| #32 | 1.8 | 336 | 182.4 | 11,178,639 | 126,110,786 | 13% |
| #6 | 2.4 | 489.6 | 201.6 | 19,798,498 | 146,019,484 | 15% |
| #7 | 1.4 | 288 | 201.6 | 11,705,056 | 157,724,440 | 16% |
| #24 | 1.7 | 355.2 | 211.2 | 15,743,753 | 173,468,393 | 17.9% |
| #19 | 2.3 | 489.6 | 211.2 | 21,738,724 | 195,407,217 | 20% |
| #20 | 2.0 | 451.2 | 220.8 | 21,997,191 | 217,404,408 | 22.4% |
| #3 | 2.2 | 480 | 220.8 | 21,410,611 | 238,715,019 | 24.6% |
| #2 | 2.0 | 441.6 | 220.8 | 19,697,762 | 258,412,781 | 26.6% |
| #46 | 2.0 | 489.6 | 240.0 | 28,200,960 | 286,713,741 | 29.5% |
| #39 | 1.6 | 384.9 | 240.0 | 22,118,600 | 308,732,141 | 31.8% |
| #10 | 1.9 | 460.8 | 240.0 | 26,442,080 | 335,374,211 | 34.5% |
| #25 | 1.4 | 345.6 | 249.6 | 21,430,935 | 356,905,156 | 36.7% |
| #33 | 1.5 | 364.8 | 249.6 | 22,731,099 | 379,632,255 | 39% |
| #36 | 2.1 | 537.6 | 259.2 | 36,114,462 | 415,750,717 | 42.8% |
| #23 | 1.9 | 489.6 | 259.2 | 32,793,600 | 448,644,317 | 46% |
| #12 | 1.7 | 460.8 | 268.8 | 33,279,385 | 481,933,702 | 49.6% |
| #15 | 1.8 | 470.4 | 268.8 | 33,993,018 | 515,926,720 | 53% |
| #21 | 1.5 | 393.6 | 268.8 | 28,438,954 | 544,365,674 | 56% |
| #28 | 1.9 | 499.2 | 268.8 | 36,068,918 | 580,434,492 | 59.7% |
| #35 | 1.7 | 460.8 | 268.8 | 33,294,385 | 613,728,977 | 63% |
| #37 | 1.7 | 528 | 307.2 | 49,728,331 | 663,457,308 | 68.2% |
| #42 | 1.4 | 432 | 307.2 | 40,768,635 | 704,325,943 | 72.6% |
| #29 | 1.6 | 499.2 | 316.8 | 50,100,730 | 754,426,773 | 77.6% |
| #14 | 1.6 | 499.2 | 316.8 | 50,100,771 | 804,427,604 | 82.7% |
| #41 | 1.9 | 672.0 | 345.6 | 80,263,249 | 884,790,753 | 91% |
| #44 | 1.6 | 595.2 | 384.0 | 87,765,712 | 972,456,665 | 100% |

K-301

| #9 | 3.9 | 259.2 | 67.2 | 1,170,406 | 1,170,406 | 0.27% |
| #4 | 3.4 | 355.2 | 105.6 | 3,960,963 | 5,131,469 | 1.2% |
| #19 | 3.0 | 310.8 | 105.6 | 3,432,751 | 8,664,210 | 2.0% |
| #31 | 2.0 | 211.2 | 105.6 | 2,355,157 | 11,019,387 | 2.5% |
| #20 | 2.8 | 316.8 | 115.2 | 4,204,265 | 15,213,652 | 3.5% |
| #18 | 3.3 | 384.0 | 115.2 | 5,096,080 | 20,319,732 | 4.7% |
| #3 | 2.1 | 240 | 115.2 | 3,185,049 | 23,404,781 | 5.4% |
| #30 | 3.2 | 403.2 | 124.8 | 6,279,756 | 29,784,637 | 6.8% |
| #40 | 3.4 | 460.8 | 134.4 | 8,323,497 | 38,108,234 | 8.8% |
| #35 | 1.8 | 240 | 134.4 | 4,335,206 | 42,443,440 | 9.8% |
| #32 | 2.6 | 345.6 | 134.4 | 6,241,698 | 48,686,137 | 11.2% |
| #27 | 2.8 | 374.4 | 134.4 | 6,762,922 | 55,449,059 | 12.8% |
| #24 | 1.4 | 192.0 | 134.4 | 3,468,155 | 58,917,214 | 13.6% |
| #8 | 2.5 | 336 | 134.4 | 6,069,279 | 64,986,413 | 15% |
| #7 | 2.6 | 345.6 | 134.4 | 6,247,698 | 71,218,211 | 16.4% |
| #6 | 1.6 | 211.2 | 134.4 | 3,715,981 | 75,044,192 | 17.3% |
| #15 | 2.9 | 393.6 | 134.4 | 7,109,739 | 82,153,931 | 19% |
| #16 | 2.6 | 374.4 | 144.0 | 7,763,458 | 89,917,489 | 20.7% |
| #33 | 1.6 | 230.4 | 144.0 | 4,777,474 | 94,695,063 | 21.8% |
| #39 | 1.5 | 211.2 | 144.0 | 4,379,443 | 99,074,406 | 22.8% |
| #11 | 2.5 | 374.4 | 153.6 | 8,733,205 | 10,790,711 | 25% |
| #2 | 1.4 | 220.8 | 163.2 | 5,730,740 | 113,788,451 | 26.2% |
| #25 | 2.2 | 355.2 | 163.2 | 9,460,482 | 123,249,033 | 28.4% |
| #42 | 3.3 | 537.6 | 163.2 | 14,318,468 | 137,467,601 | 31.6% |
| #22 | 1.7 | 288 | 172.8 | 8,499,633 | 146,157,234 | 33.6% |
| #21 | 2.7 | 460.8 | 172.8 | 13,759,415 | 159,926,649 | 36.8% |
| #14 | 1.9 | 336 | 172.8 | 10,032,906 | 169,959,455 | 39.1% |
| #13 | 1.9 | 326.4 | 172.8 | 9,746,252 | 179,705,707 | 41% |
| #12 | 1.8 | 326.4 | 182.4 | 19,759,249 | 190,465,056 | 43.8% |
| #36 | 1.8 | 326.4 | 182.4 | 10,759,249 | 201,424,305 | 46.3% |
| #37 | 1.9 | 355.2 | 182.4 | 11,717,418 | 213,241,725 | 49% |
| #26 | 1.6 | 307.2 | 192 | 11,324,620 | 224,466,246 | 51.6% |
| #28 | 1.7 | 345.6 | 201.6 | 14,046,068 | 238,612,414 | 55% |
| #29 | 1.2 | 259.2 | 211.2 | 11,461,730 | 250,174,144 | 57.5% |
| #23 | 2.0 | 412.8 | 211.2 | 18,413,116 | 268,487,270 | 61.8% |
| #17 | 1.8 | 384 | 211.2 | 16,950,067 | 285,715,759 | 65.7% |
| #5 | 2.0 | 441.6 | 220.8 | 21,429,156 | 30,244,925 | 70.7% |
| #41 | 1.8 | 403.2 | 230.4 | 21,403,433 | 328,648,458 | 75.6% |
| #1 | 2.1 | 480 | 230.4 | 25,480,397 | 354,128,755 | 81% |
| #34 | 2.2 | 518.4 | 240.0 | 29,759,740 | 383,988,695 | 88.3% |
| #10 | 1.6 | 384 | 240.0 | 22,118,400 | 406,107,095 | 93% |
| #38 | 1.8 | 460.8 | 249.6 | 28,707,914 | 434,715,008 | 100% |

K-303

| #18 | 2.5 | 240 | 96 | 2,211,740 | 2,211,740 | 0.4% |
| #09 | 2.0 | 211 | 106 | 2,352,937 | 4,464,777 | 0.9% |
| #22 | 3.8 | 403 | 106 | 4,493,998 | 9,058,775 | 1.8% |
| #27 | 2.5 | 259 | 106 | 2,788,202 | 11,946,977 | 2% |
| #07 | 1.8 | 230 | 125 | 3,482,259 | 15,429,236 | 3% |
| #15 | 2.3 | 307 | 134 | 5,445,452 | 21,074,688 | 4% |
| #05 | 1.9 | 269 | 144 | 5,477,984 | 26,552,672 | 5.4% |
| #12 | 1.6 | 230 | 144 | 4,769,270 | 31,421,952 | 6% |
| #08 | 1.4 | 230 | 163 | 6,115,775 | 37,447,727 | 7.6%0 |
| #11 | 1.8 | 288 | 163 | 7,670,661 | 45,218,488 | 9.1% |
| #13 | 1.4 | 221 | 163 | 5,786,157 | 51,104,655 | 10% |
| #24 | 2.1 | 355 | 173 | 10,600,243 | 61,704,798 | 12% |
| #16 | 2.0 | 365 | 182 | 12,143,462 | 73,748,361 | 14.8% |
| #06 | 1.4 | 250 | 182 | 8,317,440 | 82,155,701 | 17% |
| #265 | 2.0 | 374 | 192 | 13,787,136 | 95,952,937 | 19% |
| #19 | 2.4 | 480 | 202 | 19,408,429 | 115,461,365 | 23.2% |
| #23 | 1.5 | 307 | 202 | 12,477,266 | 127,938,631 | 26% |
| #30 | 1.6 | 336 | 211 | 14,987,428 | 142,926,059 | 28.7% |
| #28 | 1.6 | 346 | 211 | 15,433,482 | 158,359,441 | 32% |
| #02 | 1.7 | 384 | 221 | 18,721,014 | 177,088,455 | 35.6% |
| #03 | 1.9 | 413 | 221 | 20,134,740 | 197,215,396 | 39.6% |
| #25 | 1.6 | 355 | 221 | 17,307,187 | 214,422,483 | 43% |
| #01 | 3.0 | 720 | 240 | 41,472,000 | 255,994,483 | 51.5% |
| #19 | 2.4 | 586 | 240 | 33,753,600 | 289,748,183 | 58% |
| #29 | 1.5 | 374 | 250 | 23,300,260 | 313,048,443 | 63% |
| #17 | 1.6 | 394 | 250 | 24,464,263 | 337,494,706 | 68% |
| #04 | 1.4 | 403 | 288 | 33,426,432 | 371,021,138 | 74.6% |
| #10 | 1.8 | 528 | 288 | 43,794,432 | 414,715,470 | 83.4% |
| #20 | 1.5 | 442 | 288 | 36,661,248 | 451,476,718 | 91% |

CRYSTAL SIZE DISTRIBUTION DATA

| Crystal No. | L/w | Actual Length (L) | Actual Width (w) | (w²)(L) | Cumulative Sum of (w²)(L) | Cumulative weight % |
|---|---|---|---|---|---|---|
| #21 | 1.3 | 432 | 326 | 46,023,967 | 497,400,785 | 100% |
| K-201 | | | | | | |
| # | 1.67 | 124.5 | 57.6 | 414,056 | 414,056 | 0.06% |
| # | 2.43 | 163.2 | 67.2 | 736,785 | 1,156,741 | 0.16% |
| # | 3.18 | 336.0 | 105.6 | 3,746,756 | 4,763,697 | 0.69% |
| # | 1.91 | 201.6 | 105.6 | 2,248,114 | 7,111,711 | 1.0W. |
| # | 2.55 | 268.8 | 105.6 | 1,997,485 | 10,109,299 | 1.43% |
| # | 1.64 | 172.8 | 105.6 | 1,926,955 | 12,036,254 | 1.70% |
| # | 1.67 | 192.0 | 115.2 | 2,448,039 | 14,484,293 | 2.06% |
| K-302 | | | | | | |
| #3 | 2.4 | 182.4 | 76.8 | 1,075,739 | 1,075,739 | 0.2% |
| #5 | 4.3 | 374.4 | 86.4 | 2,794,781 | 3,770,720 | 0.7% |
| #24 | 2.8 | 240 | 86.4 | 1,791,490 | 5,662,310 | 1.0% |
| #1 | 2.3 | 259 | 115.2 | 3,439,754 | 9,102,154 | 1.7% |
| #32 | 2.7 | 307 | 115.2 | 4,076863 | 13,179,027 | 2.4% |
| #18 | 2.3 | 288 | 124.8 | 4,485,612 | 17,664,639 | 3.2% |
| #23 | 3.3 | 442 | 134.4 | 7,976,779 | 25,641,419 | 4.7% |
| #37 | 2.9 | 384 | 134.4 | 6,936,330 | 32,477,749 | 6.0% |
| #31 | 2.1 | 307 | 144 | 6,370,099 | 38,947,748 | 7.1% |
| #2 | 2.4 | 346 | 144 | 7,156,362 | 46,114,210 | 8.4% |
| #12 | 1.3 | 202 | 153.6 | 4,756,341 | 50,770,451 | 9% |
| #8 | 1.9 | 317 | 163.2 | 8,437,727 | 59,308,278 | 10.8% |
| #13 | 1.8 | 288 | 163.2 | 7,670,661 | 66,978,939 | 12.2% |
| #22 | 1.2 | 355 | 163.2 | 9,460,482 | 76,439,421 | 14% |
| #39 | 1.9 | 336 | 172.8 | 10,032,906 | 86,472,327 | 15.8% |
| #19 | 1.7 | 298 | 172.8 | 8,786,278 | 95,358,615 | 17.4% |
| #11 | 1.6 | 269 | 172.8 | 8,026,325 | 103,384,940 | 18.9% |
| #10 | 1.5 | 259 | 172.8 | 7,939,671 | 111,114,611 | 20% |
| #25 | 1.5 | 269 | 182.4 | 8,942,911 | 120,067,422 | 21.9% |
| #26 | 2.1 | 384 | 182.4 | 12,775,487 | 132,743,109 | 24.3% |
| #27 | 1.7 | 317 | 182.4 | 10,439,760 | 143,382,969 | 26.2% |
| #28 | 2.2 | 403 | 182.4 | 13,414,367 | 156,797,336 | 28.7% |
| #30 | 2.1 | 384 | 182.4 | 12,775,487 | 169,472,923 | 31% |
| #33 | 1.5 | 269 | 182.4 | 8,942,911 | 178,415,734 | 32.6% |
| #35 | 1.7 | 317 | 192 | 11,685,788 | 190,201,721 | 34.8% |
| #9 | 2.1 | 394 | 192 | 14,418,731 | 204,720,453 | 37.4% |
| #6 | 2.4 | 461 | 192 | 16,997,656 | 221,718,209 | 40.5% |
| #4 | 2.3 | 461 | 201.6 | 18,736,210 | 240,454,429 | 43.9% |
| #17 | 1.4 | 288 | 201.6 | 11,705,057 | 252,159,486 | 46% |
| #16 | 1.7 | 384 | 220.8 | 18,721,014 | 270,780,400 | 49.5% |
| #29 | 1.5 | 336 | 220.8 | 18,380,787 | 287,261,387 | 52.4% |
| #34 | 1.6 | 374 | 230.4 | 19,753,476 | 307,114,763 | 56% |
| #35 | 1.5 | 365 | 240 | 21,024,000 | 328,138,763 | 60% |
| #15 | 1.4 | 346 | 240 | 19,929,600 | 348,068,463 | 63.6% |
| #20 | 1.7 | 413 | 249.6 | 25,729,966 | 373,798,429 | 68% |
| #21 | 2.2 | 566 | 259.2 | 38,026,406 | 411,724,935 | 75% |
| #7 | 2.0 | 596 | 297.6 | 52,696,627 | 464,421,462 | 84.9% |
| #14 | 1.4 | 413 | 297.6 | 36,477,659 | 501,099,211 | 91.5% |
| #38 | 1.5 | 461 | 316.8 | 46,266,993 | 547,316,214 | 100% |
| K-201 | | | | | | |
| # | 1.70 | 326.4 | 115.2 | 4,331,667 | 18,915,960 | 2.68% |
| # | 1.93 | 259.2 | 134.4 | 4,682,022 | 23,497,982 | 3.34% |
| # | 3.33 | 480.0 | 144.0 | 9,953,270 | 33,451,262 | 4.75% |
| # | 1.87 | 268.5 | 144.0 | 5,473,736 | 39,115,098 | 5.54% |
| # | 2.00 | 288.0 | 144.0 | 5,971,968 | 45,097,066 | 6.38% |
| # | 1.73 | 249.6 | 144.0 | 5,175,705 | 50,272,721 | 7.11% |
| # | 2.13 | 307.2 | 144.2 | 6,370,099 | 56,642,720 | 8.02% |
| # | 1.76 | 288.0 | 163.2 | 7,670,661 | 64,313,431 | 9.10% |
| # | 2.35 | 384.0 | 163.2 | 10,217,448 | 74,441,079 | 10.55% |
| # | 1.50 | 259.2 | 172.8 | 7,739,670 | 82,270,749 | 11.65% |
| # | 2.00 | 345.6 | 172.8 | 10,319,460 | 92,600,309 | 13.11% |
| # | 2.78 | 480.0 | 172.8 | 14,332,723 | 106,933,032 | 15.14% |
| # | 1.75 | 336.0 | 192.0 | 12,386,304 | 119,319,336 | 16.89% |
| # | 1.75 | 336.0 | 192.0 | 12,386,304 | 131,705,640 | 18.66% |
| # | 1.75 | 336.0 | 192.0 | 12,386,304 | 144,091,944 | 20.39% |
| # | 1.52 | 307.2 | 201.6 | 12,495,394 | 156,477,338 | 22.16% |
| # | 1.90 | 384.0 | 201.6 | 15,606,743 | 172,184,081 | 24.37% |
| # | 1.45 | 307.2 | 211.2 | 13,702,791 | 185,786,772 | 26.63% |
| # | 2.14 | 451.2 | 211.2 | 20,115,974 | 206,012,746 | 29.16% |
| # | 1.67 | 384.0 | 230.4 | 20,384,317 | 226,327,153 | 32.03% |
| # | 1.72 | 480.0 | 278.4 | 37,203,148 | 263,430,311 | 37.30% |
| # | 1.70 | 489.6 | 288.0 | 40,609,381 | 304,134,692 | 43.05% |
| # | 1.50 | 432.0 | 288.0 | 35,731,708 | 339,971,400 | 48.12% |
| # | 1.33 | 384.0 | 288.0 | 31,750,496 | 371,721,996 | 52.12% |
| # | 1.34 | 451.2 | 336.0 | 50,938,625 | 422,760,621 | 59.98% |
| # | 1.19 | 480.0 | 403 | 78,033,715 | 500,794,350 | 70.9% |
| # | 1.33 | 537.6 | 403.2 | 87,397,761 | 588,192,091 | 83.3% |
| # | 1.21 | 556.8 | 460.5 | 118,219,041 | 706,421,138 | 100% |
| K-202 | | | | | | |
| #33 | 1.50 | 288 | 76.8 | 7,156,361 | 7,156,361 | 0.1% |
| #34 | 2.50 | 192.0 | 76.8 | 1,485,446 | 8,751,707 | 1.2% |
| #6 | 2.80 | 268.8 | 96.0 | 2,477,260 | 11,219,067 | 1.6% |
| #12 | 1.67 | 172.8 | 105.6 | 1,926,955 | 13,156,022 | 1.9% |
| #30 | 1.73 | 182.4 | 105.6 | 2,034,008 | 26,419,097 | 3.7% |
| #45 | 2.50 | 288.0 | 115.2 | 3,722,059 | 30,241,156 | 4.3% |
| #21 | 3.42 | 393.6 | 115.2 | 5,213,481 | 35,464,637 | 5.0% |
| #35 | 1.54 | 192.0 | 124.8 | 2,990,407 | 38,455,044 | 5.6% |
| #11 | 2.05 | 278.4 | 134.4 | 5,028,739 | 43,483,783 | 6.1% |
| #2 | 1.80 | 259.2 | 144.0 | 5,374,771 | 48,758,654 | 6.9% |
| #9 | 2.00 | 288.0 | 144.0 | 5,971,968 | 54,730,622 | 7.7% |
| #32 | 2.40 | 345.6 | 144.0 | 7,156,361 | 61,996,983 | 8.7% |
| #44 | 1.94 | 297.6 | 144.0 | 6,171,033 | 68,158,016 | 9.6% |
| #7 | 2.00 | 307.2 | 153.6 | 7,243,038 | 75,411,054 | 10.6% |
| #36 | 2.19 | 336.0 | 153.6 | 7,927,234 | 83,338,278 | 11.7% |
| #43 | 1.94 | 297.6 | 152.6 | 7,021,269 | 90,359,457 | 12.7% |
| #47 | 3.14 | 480.0 | 153.6 | 1,324,620 | 101,684,177 | 14.3% |
| #5 | 1.94 | 336 | 163.2 | 8,437,727 | 110,111,904 | 15.5% |
| #20 | 1.71 | 278.4 | 163.2 | 7,414,972 | 117,436,776 | 16.5% |
| #28 | 2.10 | 345.6 | 163.2 | 9,204,793 | 126,741,669 | 17.8% |
| #46 | 2.12 | 345.6 | 163.2 | 9,204,793 | 135,946,462 | 19.1% |
| #27 | 2.06 | 355.2 | 172.8 | 10,606,215 | 146,452,677 | 20.6% |
| #31 | 2.06 | 355.2 | 172.8 | 10,606,215 | 157,158,792 | 22.1% |
| #19 | 1.84 | 336.0 | 182.4 | 11,178,639 | 168,337,431 | 23.6% |
| #1 | 1.85 | 355.2 | 192.0 | 13,094,092 | 181,431,623 | 25.5% |
| #3 | 1.75 | 336.0 | 192.0 | 12,386,304 | 193,717,927 | 27.2% |
| #10 | 2.15 | 412.8 | 192.0 | 15,217,459 | 209,035,381 | 29.4% |
| #14 | 1.80 | 345.1 | 192.0 | 12,740,198 | 221,775,484 | 31.1% |
| #15 | 1.75 | 336.0 | 192.0 | 12,386,304 | 234,151,784 | 32.9% |
| #48 | 1.46 | 280.0 | 192.0 | 10,321,920 | 234,172,209 | 32.9% |
| #24 | 1.90 | 384.0 | 201.6 | 15,606,743 | 249,778,952 | 35.1% |
| #25 | 1.71 | 345.6 | 201.6 | 14,046,068 | 263,725,020 | 37.1% |
| #29 | 1.43 | 288.0 | 201.6 | 11,705,057 | 275,430,079 | 38.7% |
| #39 | 1.52 | 307.2 | 201.6 | 12,485,394 | 288,015,473 | 40.4% |
| #23 | 1.82 | 384.0 | 211.2 | 17,118,488 | 305,143,961 | 42.9% |
| #41 | 1.45 | 307.2 | 211.2 | 13,702,291 | 318,746,752 | 44.8% |
| #13 | 1.73 | 384.0 | 220.8 | 18,721,013 | 337,467,765 | 47.4% |
| #49 | 1.61 | 355.2 | 220.8 | 17,316,937 | 354,784,702 | 49.8% |
| #4 | 1.76 | 422.4 | 240.0 | 24,330,240 | 379,214,942 | 53.3% |
| #8 | 1.60 | 384.0 | 240.0 | 22,118,200 | 401,333,342 | 56.4% |
| #12 | 1.53 | 384.0 | 249.6 | 23,923,261 | 425,256,603 | 59.7% |
| #18 | 1.62 | 422.4 | 259.2 | 28,378,791 | 453,635,394 | 63.7% |
| #26 | 1.59 | 412.8 | 259.2 | 27,733,719 | 481,369,213 | 67.6% |
| #22 | 1.74 | 374.4 | 268.8 | 27,051,687 | 509,420,900 | 71.5% |
| #42 | 1.68 | 451.2 | 268.8 | 32,600,752 | 541,021,652 | 76% |
| #50 | 1.36 | 364.8 | 268.8 | 26,358,054 | 567,379,206 | 79.7% |
| #17 | 1.83 | 528.0 | 288.0 | 43,794,432 | 611,174,138 | 85.8% |
| #37 | 1.47 | 422.4 | 288.0 | 35,035,465 | 646,209,683 | 90.7% |
| #38 | 1.17 | 336.0 | 288.0 | 27,469,184 | 674,078,767 | 94.7% |
| #40 | 1.31 | 403.2 | 307.2 | 78,050,725 | 712,119,492 | 100% |
| K-203 | | | | | | |
| #35 | 2.14 | 144 | 67.2 | 650,270 | 650,270 | 0.135% |
| #22 | 2.38 | 182.4 | 76.8 | 1,075,738 | 1,726,118 | 0.39% |
| #30 | 1.78 | 153.6 | 86.4 | 1,146,617 | 2,772,735 | 0.60% |
| #32 | 2.50 | 240.0 | 96.0 | 2,211,740 | 5,084,475 | 1.06% |
| #29 | 2.50 | 240.0 | 96.0 | 2,211,740 | 7,296,415 | 1.52% |
| #18 | 1.50 | 144.0 | 96.0 | 1,327,104 | 8,623,419 | 1.79% |
| #4 | 2.00 | 192.0 | 96.0 | 1,769,472 | 10,392,991 | 2.16% |
| #27 | 1.82 | 192.0 | 105.6 | 2,141,061 | 12,434,052 | 2.61% |
| #33 | 3.00 | 316.8 | 105.6 | 3,432,470 | 16,066,702 | 3.34% |

-continued

CRYSTAL SIZE DISTRIBUTION DATA

| Crystal No. | L/w | Actual Length (L) | Actual Width (w) | (w²)(L) | Cumulative Sum of (w²)(L) | Cumulative weight % |
|---|---|---|---|---|---|---|
| #21 | 2.77 | 345.6 | 124.8 | 5,382,733 | 21,449,435 | 4.46% |
| #28 | 2.00 | 249.0 | 124.8 | 3,787,429 | 25,337,064 | 5.27% |
| #11 | 2.57 | 345.6 | 134.4 | 6,242,697 | 31,479,761 | 6.57% |
| #16 | 1.53 | 220.8 | 144.0 | 4,478,408 | 36,158,26.9 | 7.52% |
| #5 | 2.06 | 316.8 | 153.6 | 7,474,249 | 43,632,419 | 9.08% |
| #17 | 1.50 | 230.4 | 153.6 | 5,435,717 | 49,068,335 | 10.21% |
| #31 | 1.56 | 240.0 | 153.6 | 5,662,310 | 54,730,645 | 11.38% |
| #3 | 3.12 | 508.8 | 163.2 | 13,451,401 | 68,272,146 | 14.20% |
| #6 | 2.47 | 393.6 | 163.2 | 10,483,236 | 78,765,382 | 16.38% |
| #9 | 1.56 | 268.8 | 172.8 | 8,026,324 | 86,291,706 | 18.05% |
| #10 | 1.50 | 259.2 | 172.8 | 7,739,670 | 94,431,376 | 19.66% |
| #19 | 1.83 | 316.8 | 172.8 | 9,459,497 | 103,990,973 | 21.63% |
| #23 | 2.33 | 403.2 | 172.8 | 12,039,487 | 116,030,460 | 24.14% |
| #26 | 2.28 | 393.6 | 172.8 | 11,752,733 | 127,783,293 | 26.58% |
| #24 | 2.20 | 422.4 | 192.0 | 15,471,353 | 143,354,946 | 29.82% |
| #15 | 1.43 | 288.0 | 201.6 | 11,705,057 | 155,059,703 | 32.25% |
| #25 | 1.95 | 412.8 | 211.2 | 18,413,115 | 173,422,728 | 36.08% |
| #20 | 1.61 | 355.2 | 220.8 | 17,316,937 | 190,789,765 | 39.69% |
| #14 | 1.71 | 393.6 | 230.4 | 20,793,925 | 211,683,690 | 44.03% |
| #34 | 1.71 | 393.6 | 230.4 | 20,793,925 | 232,477,615 | 48.38% |
| #7 | 1.70 | 441.6 | 259.2 | 29,668,737 | 262,246,352 | 54.55% |
| #2 | 1.93 | 537.6 | 278.4 | 41,667,426 | 303,913,778 | 63.22% |
| #8 | 1.72 | 480.0 | 278.4 | 37,203,148 | 341,117,026 | 70.96% |
| #12 | 1.33 | 384.0 | 288.0 | 31,750,496 | 372,917,422 | 77.58% |
| #1 | 1.51 | 480.8 | 316.8 | 48,173,775 | 421,141,394 | 87.60% |
| #13 | 1.57 | 528.0 | 336.0 | 59,619,088 | 480,750,485 | 100.00% |

Lab Experiments 150 grams of an adduct solid containing approximately 30 weight percent phenol and 70 weight percent bisphenol A were charged to a 2 liter, 5 neck glass pot. The glass pot included a heating mantle, a steam generator, a sparger, and an overhead condenser and receiver. 150 grams of water were added to the adduct solid, and the temperature of the mixture was slowly increased. The mixture was completely liquefied to form an adduct solution when its temperature reached 60° C. The heating of the solution was continued slowly, and steam sparging was performed on the solution when its temperature approached 100° C. The condensate received in the overhead receiver was observed to appear milky, indicating a significant presence of phenol in the overhead receiver. Sparging was continued until the condensate collected in the overhead receiver ceased to appear milky. A sample was taken from the solution in the glass pot and analyzed to reveal a residual phenol content of about 5 weight percent. Steam sparging was continued until a sample of the solution in the glass pot was analyzed to reveal a residual phenol content of less than 1 weight percent. At this time, about 400 grams of condensate had been collected in the overhead receiver and the water content of the solution in the glass pot exceeded about 20 weight percent.

About 200 grams of water at a temperature of about 100° C. was added to the solution in the glass pot, and the mixture was agitated and slowly cooled. A dense cloud of crystals was observed when the temperature of the agitated solution reached a temperature of about 98° C. The level of agitation was increased and a portion of the agitated solution spilled through a large outlet on the side of the glass pot into a vacuum filter. Crystals were recovered in the filter and washed with water at a temperature of about 100° C. in the filter. The washed crystals were large, well-shaped rhombic crystals having an average length of 2 to 3 millimeters and a width of 1 to 1.5 millimeters, with some crystals being 4 to 5 millimeters long and about 3 millimeters wide. The crystals were partially dried overnight in an oven at a temperature of about 100° C. and analyzed by vapor pressure chromatography. The analysis indicated a content of impurities of about 175 ppm, with non-detectable levels of phenol and the o,p isomer of bisphenol A. A subsequent analysis of the sample by a different method yielded the following concentrations of impurities:

| Impurity | Concentration (ppm) |
|---|---|
| phenol | non-detectable |
| o,p isomer of bisphenol A | 61 |
| trisphenol 2 | 9 |
| spirobiindane | 90 |
| isopropenyl phenol trimer | 240 |
| unknown impurities | 49 |
| Total | 449 |

The trisphenol 2, spirobiindane, and isopropenylphenol trimer are suspected of being contaminants from the Indian plant phenol which at the time was severely back-contaminated with impurities from the catalytic cracking system.

It is expected that incorporation of a low temperature process such as the one described above to result in improved purity of product. The product is expected to have improved performance in producing high clarity polycarbonate resins compared to BPA produced in many other systems. It is further expected that the process described herein will not be significantly impacted by thermal and catalytic decomposition of the BPA product. It is expected that the BPA product will have a much lower rate of formation of impurities and color throughout the entire process. The rate of formation of impurities in the process may be so low as to increase the useful operational time of any given reactor bed between replacement or cleanup of the bed. The incorporation of a catalytic cracking system may become obsolete because the rate of formation of impurities may be so low that the reactor beds can absorb the impurities formed over a one to two year period at which time the beds may be washed with a wet phenol solution to release the heavy impurities for purge before re-commissioning the reactor.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements and compositions described herein or in the features or in the sequence of features of the methods described herein without departing from the spirit and scope of the invention as described in the following claims.

I claim:

1. A system for preparing a relatively high-purity bisphenol A product from an adduct solid while inhibiting decomposition of bisphenol A, the adduct solid comprising at least about 25 weight percent phenol, the system comprising:

a) a first solidification system producing a bisphenol A adduct solid from a first mixture of bisphenol A and phenol during use, the adduct solid comprising at least about 25 weight percent phenol, and the first solidification system operating at a temperature below 150° C.;

b) a first recovery system separating at least a portion of the adduct solid from the first mixture during use, the first recovery system operating at a temperature below 150° C.;

c) a mixing system heating water to a temperature less than about 150° C. during use, and mixing the adduct solid with the heated water during use to form a first solution comprising bisphenol A, water, and phenol;

d) a separation column adapted to reduce the concentration of phenol in the first solution and produce a second solution comprising bisphenol A and less than about 1 weight percent phenol during use, the column comprising an overhead outlet near the top of the column, a bottoms outlet near the bottom of the column, and a feed inlet between the overhead outlet and the bottoms outlet, and the column operating at a temperature below about 150° C. during use;

e) a second solidification system adapted to produce a bisphenol A product from the second solution during use, the second solidification system operating at a temperature below about 150° C. during use; and f) a second recovery system adapted to separate at least a portion of the bisphenol A product from the second solution during use, the separated portion comprising at least about 99 weight percent bisphenol A, the second recovery system operating at a temperature below about 150° C. during use.

2. The system of claim 1, further comprising a distribution tray located within the column and a feed distributor located within the column, and wherein a recycle conduit is connected to the column to recycle at least a portion of a bottoms stream from the bottoms outlet into the column at a point between the distribution tray and the feed distributor.

3. The system of claim 1, further comprising a reactor producing the first mixture from the reaction of phenol and acetone during use.

4. The system of claim 1, further comprising a heated water injection system injecting heated water into the column during use.

5. The system of claim 1, further comprising a heated water injection system injecting heated water into the column during use, and wherein the heated water is in the form of steam.

6. The system of claim 1, further comprising a steam injection system adapted to inject steam into the column during use, and wherein the steam injection system comprises a steam injection port located near the bottom of the column.

7. The system of claim 1, further comprising a tray located in the column below a feed distributor in the column, the tray adapted to screen solids and inhibit at least a portion of solids from entering a bottoms stream during use.

8. The system of claim 1, further comprising a feed distributor within the column, and wherein the column comprises packing between the feed distributor and the bottoms outlet.

9. The system of claim 1, further comprising a steam system injecting steam into a column feed stream at a location upstream of the column during use.

10. The system of claim 1, further comprising a heating system heating at least a portion of the column wall during use.

11. The system of claim 1, further comprising a distributor located within the column and adapted to distribute a column feed stream substantially parallel to the column wall during use.

12. The system of claim 1 wherein the mixing system comprises a vessel with an agitator.

13. The system of claim 1 wherein the first recovery system comprises at least one screen bowl centrifuge and a phenol wash system to wash solids during use.

14. The system of claim 1 wherein the second solidification system comprises a draft-tube crystallizer.

15. The system of claim 1 wherein the second solidification system comprises a draft-tube crystallizer, and further comprising a vacuum system adapted to maintain the draft-tube crystallizer at an absolute pressure between about 500 torr and about 700 torr during use.

16. The system of claim 1 wherein the second solidification system comprises a draft-tube crystallizer, and further comprising a cooler adapted to maintain the temperature within the draft-tube crystallizer between about 90° C. and about 100° C. during use.

17. The system of claim 1, wherein the second recovery unit comprises at least one pusher centrifuge and a water wash system to wash solids during use.

18. The system of claim 1, wherein the second recovery unit comprises at least one contact dryer and a steam system heating the heat transfer surface of the dryer during use.

19. The system of claim 1, wherein the mixing system is adapted to heat the water to a temperature greater than about 60° C. and less than about 90° C. during use.

20. The system of claim 1, wherein the first solidification system comprises a crystallizer adapted to maintain a stream at a temperature greater than about 40° C. and less than about 60° C. during use.

21. The system of claim 1, wherein the first solidification system comprises a crystallizer and wherein the crystallizer comprises a conduit loop, the conduit loop comprising a solidification zone that communicates with a heat exchanger.

22. The system of claim 1, further comprising a steam injection system adapted to inject steam into the column during use, and wherein the steam injection system comprises a steam injection port located near the bottom of the column, and further comprising a control system adapted to monitor the phenol concentration in a bottoms stream and adjust the amount of steam injected into the column as a function of the phenol concentration in the bottoms stream during use.

23. The system of claim 1, further comprising a steam system adapted, during use, to inject steam into a column feed stream at a location upstream of the column, and wherein the steam injection system is adapted to inject steam having a pressure greater than about 50 psia and less than about 155 psia during use.

24. The system of claim 1, further comprising a heating system adapted to heat at least a portion of the column wall to a temperature of greater than about 110° C. and less than about 150° C. during use.

25. The system of claim 1, further comprising a heating system adapted to heat the adduct solution to a temperature of less than about 150° C. during use, prior to the introduction of the adduct solution into the column.

26. The system of claim 1 wherein the mixing system further comprises a vessel, and wherein the heating system comprises a shell and tube heat exchanger located downstream of the vessel.

27. The system of claim 1 wherein the mixing system further comprises coils, the coils being adapted to heat the adduct solids within the vessel to a temperature of less than about 150° C. during use.

28. The system of claim 1 wherein the second solidification system comprises a draft-tube crystallizer, and further comprising a water system adapted to add water to the draft-tube crystallizer at a selected temperature during use to maintain the temperature of a stream within the crystallizer at a selected temperature during use.

29. The system of claim 1 wherein the second solidification system comprises a draft-tube crystallizer, and further comprising a water system adapted to add water to the draft-tube crystallizer to maintain the composition of a stream within the crystallizer at 40–60 weight percent water and 40–60 weight percent bisphenol A.

30. A system for separating phenol from a bisphenol A adduct solid while inhibiting decomposition of bisphenol A, the adduct solid comprising at least about 25 weight percent phenol, the system comprising:

a) a mixing system adapted to heat water to a temperature less than about 150° C. and mix the adduct solid with the heated water to form a first solution comprising bisphenol A, water, and phenol;

b) a conduit connected to allow the first solution to flow to a separation column, the separation column being adapted to receive the first solution from the mixer and adapted to reduce the concentration of phenol in the first solution to produce a second solution comprising bisphenol A and less than about 1 weight percent phenol, the column comprising an overhead outlet near the top of the column, a bottoms outlet near the bottom of the column, and a feed inlet between the overhead outlet and the bottoms outlet.

31. The system of claim 1, further comprising a control system controlling the amount of heated water mixed with the adduct solution during use as a function of the rate of a stream comprising phenol and bisphenol A entering the first recovery system.

32. The system of claim 1, further comprising a control system controlling the amount of heated water mixed with the adduct solution during use as a function of the rate that the adduct solution exits the mixing system.

33. The system of claim 1 further comprising a control system controlling the amount of water during use that is added to a bottoms recycle stream comprising bisphenol A and water, the amount of water added being controlled as a function of properties of a column bottoms stream.

34. A system for preparing a relatively high-purity bisphenol A product from an adduct solid while inhibiting decomposition of bisphenol A, the adduct solid comprising at least about 25 weight percent phenol, the system comprising:

a) a first solidification system producing a bisphenol A adduct solid from a first mixture of bisphenol A and phenol during use, the adduct solid comprising at least about 25 weight percent phenol, and the first solidification system operating at a temperature below 150° C.;

b) a first recovery system separating at least a portion of the adduct solid from the first mixture during use, the first recovery system operating at a temperature below 150° C.;

c) a mixing system adapted to melt the adduct solid and add water at a temperature less than about 150° C. to the melted adduct solid during use to form a first solution comprising bisphenol A, water, and phenol;

d) a separation column adapted to reduce the concentration of phenol in the adduct solution and produce a second solution comprising bisphenol A and less than about 1 weight percent phenol during use, the column comprising an overhead outlet near the top of the column, a bottoms outlet near the bottom of the column, and a feed inlet between the overhead outlet and the bottoms outlet, and the column operating at a temperature below about 150° C. during use;

e) a second solidification system adapted to produce a bisphenol A product from the second solution during use, the second solidification system operating at a temperature below about 150° C. during use; and f) a second recovery system adapted to separate at least a portion of the bisphenol A product from the second solution during use, the separated portion comprising at least about 99 weight percent bisphenol A, the second recovery system operating at a temperature below about 150° C. during use.

\* \* \* \* \*

UNITED STATES PATENT AND TRADEMARK OFFICE
CERTIFICATE OF CORRECTION

PATENT : 6,033,635
DATED : March 7, 2000
INVENTOR(S) : Ben Gammill

It is certified that error appears in the above-identified patent and that said Letters Patent is hereby corrected as shown below:

In the Title:

Before "System", delete "Method and" --

In the Related U.S. Application Data:

Change the phrase, "Division of application No. 08/632,663, Apr. 15, 1996..." and substitute therefore -- "Division of application No. 08/632,663, Apr. 12, 1996" --

Col. 1, line 1, in the title, before "System", delete "Method and" --

Col. 1, line 5, change the phrase, "filed April 15, 1996..." and substitute therefore -- "filed April 12, 1996" --

Signed and Sealed this

Fifteenth Day of May, 2001

*Attest:*

NICHOLAS P. GODICI

*Attesting Officer*  *Acting Director of the United States Patent and Trademark Office*